United States Patent
Handler

(10) Patent No.: US 11,386,994 B2
(45) Date of Patent: Jul. 12, 2022

(54) OPTIMIZED BEDSIDE SAFETY PROTOCOL SYSTEM

(71) Applicants: Baxter International Inc., Deerfield, IL (US); BAXTER HEALTHCARE SA, Glattpark (CH)

(72) Inventor: Jonathan Alan Handler, Northbrook, IL (US)

(73) Assignees: Baxter International Inc., Deerfield, IL (US); BAXTER HEALTHCARE SA, Glattpark (CH)

(*) Notice: Subject to any disclaimer, the term of this patent is extended or adjusted under 35 U.S.C. 154(b) by 314 days.

(21) Appl. No.: 16/165,528

(22) Filed: Oct. 19, 2018

(65) Prior Publication Data

US 2019/0122764 A1  Apr. 25, 2019

Related U.S. Application Data

(60) Provisional application No. 62/574,529, filed on Oct. 19, 2017.

(51) Int. Cl.
*G16H 40/63* (2018.01)
*G16H 40/60* (2018.01)
(Continued)

(52) U.S. Cl.
CPC .......... *G16H 40/63* (2018.01); *A61B 5/0022* (2013.01); *A61B 5/02055* (2013.01);
(Continued)

(58) Field of Classification Search
CPC .... A61B 5/4836; A61B 5/746; A61M 5/1407; A61M 5/1413; A61M 5/172;
(Continued)

(56) References Cited

U.S. PATENT DOCUMENTS 5,713,856 A * 2/1998 Eggers ............... H01R 13/7038
604/65
6,830,549 B2  12/2004 Bui et al.
(Continued)

FOREIGN PATENT DOCUMENTS

AU  2017279693 A1  12/2017
CA  2548987 A1  11/2001
(Continued)

OTHER PUBLICATIONS

Preliminary Report on Patentability for related International Application No. PCT/US2018/056741; report dated Apr. 21, 2020; (12 pages).
(Continued)

*Primary Examiner* — Kami A Bosworth
(74) *Attorney, Agent, or Firm* — K&L Gates LLP

(57) ABSTRACT

Therapy device systems, modules, and methods, include memory, one or more processors, in communication with the memory, a plurality of medical therapy devices, a plurality of patient monitoring devices, and a protocol execution module, configured to execute on the one or more processors. The protocol execution module displays a plurality of protocols. The protocol execution module receives a selected protocol, associated with an individual medical therapy device being one of a plurality of medical therapy devices and associated with an individual patient monitoring device being one of a plurality of patient monitoring devices. The protocol execution module executes the selected protocol with the individual medical therapy device.

16 Claims, 24 Drawing Sheets

(51) Int. Cl.

| | | |
|---|---|---|
| *A61M 16/00* | (2006.01) | |
| *G16H 20/17* | (2018.01) | |
| *A61B 5/00* | (2006.01) | |
| *A61B 5/0205* | (2006.01) | |
| *A61M 5/172* | (2006.01) | |
| *A61N 1/39* | (2006.01) | |
| *A61B 5/021* | (2006.01) | |
| *A61B 5/024* | (2006.01) | |
| *A61B 5/0295* | (2006.01) | |
| *A61B 5/08* | (2006.01) | |
| *A61B 5/103* | (2006.01) | |
| *A61B 5/145* | (2006.01) | |
| *A61B 5/1455* | (2006.01) | |
| *A61M 1/14* | (2006.01) | |
| *A61N 1/02* | (2006.01) | |

(52) U.S. Cl.
CPC ............ *A61B 5/746* (2013.01); *A61M 5/172* (2013.01); *A61M 16/024* (2017.08); *A61N 1/39* (2013.01); *G16H 20/17* (2018.01); *G16H 40/60* (2018.01); *A61B 5/021* (2013.01); *A61B 5/024* (2013.01); *A61B 5/0295* (2013.01); *A61B 5/08* (2013.01); *A61B 5/1036* (2013.01); *A61B 5/14532* (2013.01); *A61B 5/14551* (2013.01); *A61B 2562/0247* (2013.01); *A61M 1/14* (2013.01); *A61N 1/025* (2013.01)

(58) Field of Classification Search
CPC ........ A61M 5/1723; A61M 2005/1726; A61M 2205/18; A61M 2205/183; A61M 2205/186; A61M 2205/3303; A61M 2205/3561; A61M 2205/3569; A61M 2205/50; A61M 2205/502; A61M 2205/505; A61M 2230/005; G16H 20/17; G16H 40/60; G16H 40/63
See application file for complete search history.

(56) References Cited

U.S. PATENT DOCUMENTS

| | | | |
|---|---|---|---|
| 6,899,103 B1 | 5/2005 | Hood et al. | |
| 7,483,756 B2 | 1/2009 | Engleson et al. | |
| 8,554,480 B2 | 10/2013 | Grigsby et al. | |
| 8,600,777 B2 | 12/2013 | Schoenberg et al. | |
| 8,617,135 B2 | 12/2013 | Rinehart et al. | |
| 9,022,974 B2 | 5/2015 | Rinehart et al. | |
| 9,272,090 B2 | 3/2016 | Salinas et al. | |
| 9,436,645 B2 | 9/2016 | Al-Ali et al. | |
| 2003/0095150 A1* | 5/2003 | Trevino | G01R 33/546 715/810 |
| 2004/0034284 A1 | 2/2004 | Aversano et al. | |
| 2005/0177096 A1* | 8/2005 | Bollish | A61B 5/4821 604/65 |
| 2007/0055460 A1* | 3/2007 | Jung | G16B 20/00 702/20 |
| 2007/0180140 A1 | 8/2007 | Welch et al. | |
| 2008/0126132 A1 | 5/2008 | Warner et al. | |
| 2008/0139898 A1 | 6/2008 | Johnson et al. | |
| 2014/0111335 A1 | 4/2014 | Kleiss et al. | |
| 2014/0172459 A1 | 6/2014 | Devries et al. | |
| 2014/0202455 A1 | 7/2014 | Garde et al. | |
| 2015/0137988 A1 | 5/2015 | Gravenstein et al. | |
| 2015/0186607 A1 | 7/2015 | Gelijinse et al. | |
| 2015/0238270 A1* | 8/2015 | Ratty | A61B 34/10 600/407 |
| 2015/0238692 A1 | 8/2015 | Peterson et al. | |
| 2015/0257698 A1 | 9/2015 | Spratt et al. | |
| 2015/0363566 A1 | 12/2015 | Johnson et al. | |
| 2017/0071549 A1 | 3/2017 | Seely et al. | |
| 2020/0114077 A1* | 4/2020 | Gholami | A61M 5/172 |
| 2021/0016001 A1* | 1/2021 | Kircher, Jr. | G16H 50/50 |

FOREIGN PATENT DOCUMENTS

| | | | |
|---|---|---|---|
| CA | 2490284 A1 | 8/2003 | |
| CN | 105286801 A | 2/2016 | |
| CN | 105678092 A | 6/2016 | |
| WO | 96/28209 A1 | 9/1996 | |
| WO | 2014/100687 A1 | 6/2014 | |
| WO | 2014/210465 A1 | 12/2014 | |
| WO | 2017/030976 A1 | 2/2017 | |
| WO | 2018/112354 A1 | 6/2018 | |

OTHER PUBLICATIONS

International Search Report and Written Opinion for related International Application No. PCT/US2018/056741; report dated Feb. 5, 2019; (21 pages).

Written Opinion for related Singapore Application No. 11202003491R; action dated Dec. 13, 2021; (11 pages).

* cited by examiner

OPTIMIZED BEDSIDE SAFETY PROTOCOL SYSTEM

PRIORITY CLAIM

This application claims priority to U.S. Provisional Application No. 62/574,529, entitled "BEDSIDE CLOSED LOOP THERAPY SYSTEM WITH SPECIAL OPTIMIZATION FOR RESCUE," filed Oct. 19, 2017, the entire contents of which are incorporated herein by reference and relied upon.

BACKGROUND

In typical hospital settings, patients are often left alone. For example, most of the time a sick patient is in a hospital, the patient is not being actively monitored by a clinician in the patient's room. Most hospitals therefore employ "rapid response" teams, to identify and treat any rapidly deteriorating patients. Likewise, in typical hospital settings today, care is being shifted toward lower cost and/or less trained staff. For example, hospitalists are pushing patient care to mid-level providers; nurses are spending less and less time on patient care.

Accordingly, systems and methods are needed to make patient monitoring and related care both safer and more cost effective.

SUMMARY

The systems and methods disclosed herein may include a bedside therapy system (also referred to herein as "bedside brain") in communication with a bedside brain server, a patient, a plurality of patient monitoring devices, and a plurality of patient therapy devices.

Generally, bedside brain is intended to be a backup to nursing staff, and act as the first responder for rapid response teams. The purpose of the bedside brain is to monitor patient data (e.g., vital signs, lab results, etc.) via patient monitoring devices, determine the appropriate decision support guidance/alerts/notifications, including particular actions to be taken by patient therapy devices based on an internal rules engine with structure determined by a "rule specification" (also referred to herein as "rule protocol", "safety protocol", or "protocol"), display appropriate decision support guidance/alerts/notifications, and execute the particular action with the patient therapy devices. Safety protocols may be generally defined as short term, emergency intervention protocols, to at least prevent or reverse an ongoing clinical state of degradation, which may be exacerbated by an ongoing therapy. Typically, safety protocols will occur after a predetermined amount of time for a warning has passed. The bedside brain may display vital signs and trends, as selected by a clinician. The bedside brain activates an alarm to alert a clinician if vital signs are outside of bedside brain safe operating ranges.

Preferably, the bedside brain is configured to execute a therapeutic control rule (e.g., selected by a clinician), read patient monitors, EMR data etc. and control therapeutic devices. The control rule may be specified in a manner that allows a "rule specification" element to fully configure and specify the control algorithm, limits, and verification parameters. The bedside brain is further configured to warn a clinician when vital signs are outside of specified ranges and/or devices need attention. The bedside brain is further configured to maintain full functionality (with exception of access to server data) when disconnected from higher level hospital systems. The bedside brain is further configured to store and retrieve data from internal data stores. The bedside brain is further configured to support a global multi-lingual human interface.

In light of the disclosure herein, and without limiting the scope of the invention in any way, in a first aspect of the present disclosure, which may be combined with any other aspect listed herein unless specified otherwise, a system includes a memory, one or more processors, in communication with the memory, a plurality of medical therapy devices, a plurality of patient monitoring devices, and a protocol execution module. The protocol execution module is configured to execute on the one or more processors, to display a plurality of protocols, and receive, from a user, a selected protocol. The selected protocol is associated with an individual medical therapy device, being one of the plurality of medical therapy devices, and associated with an individual patient monitoring device, being one of the plurality of patient monitoring devices. The individual medical therapy device receives, from the user, a first confirmation of the selected protocol. The protocol execution module receives, from the user, a second confirmation of the selected protocol. The protocol execution module executes the selected protocol with the individual medical therapy device.

In a second aspect of the present disclosure, which may be combined with any other aspect listed herein unless specified otherwise, the plurality of medical therapy devices includes at least one of an infusion pump, a dialysis or renal failure therapy machine, a respirator, and a defibrillators.

In a third aspect of the present disclosure, which may be combined with any other aspect listed herein unless specified otherwise, the plurality of patient monitoring devices includes at least one of a heart rate sensor, a temperature sensor, a pulse oximetry sensor, a patient weight sensor, a glucose sensor, a respiratory sensor, a blood pressure sensor, a pressure sensor, and a volume-index sensor.

In a fourth aspect of the present disclosure, which may be combined with any other aspect listed herein unless specified otherwise, the protocol execution module receives the plurality of protocols from an external server.

In a fifth aspect of the present disclosure, which may be combined with any other aspect listed herein unless specified otherwise, executing the selected protocol with the individual medical therapy device includes identifying a patient parameter with the individual patient monitoring device, and determining that the patient parameter violates a threshold, wherein the threshold is dictated by the selected protocol.

In a sixth aspect of the present disclosure, which may be combined with any other aspect listed herein unless specified otherwise, executing the selected protocol with the individual medical therapy device further includes, responsive to determining that the patient parameter violates the threshold, triggering an alarm.

In a seventh aspect of the present disclosure, which may be combined with any other aspect listed herein unless specified otherwise, further comprising, responsive to triggering the alarm, displaying, at the protocol execution module, an action dictated by the selected protocol In a eighth aspect of the present disclosure, which may be combined with any other aspect listed herein unless specified otherwise, further including starting a countdown timer.

In a ninth aspect of the present disclosure, which may be combined with any other aspect listed herein unless specified otherwise, the countdown timer expires, such that the protocol execution module instructs the individual medical therapy device to take the action, and wherein the individual medical therapy device takes the action.

In a tenth aspect of the present disclosure, which may be combined with any other aspect listed herein unless specified otherwise, the individual medical therapy device is an infusion pump, and wherein the action is one of increasing infusion rate of the infusion pump, decreasing infusion rate of the infusion pump, and ceasing infusion.

In a eleventh aspect of the present disclosure, which may be combined with any other aspect listed herein unless specified otherwise, prior to the countdown timer expiring, the user instructs the protocol execution module to take the action, and the protocol execution module instructs the individual medical therapy device to take the action, such that the individual medical therapy device takes the action.

In a twelfth aspect of the present disclosure, which may be combined with any other aspect listed herein unless specified otherwise, prior to the countdown timer expiring, the user instructs the protocol execution module to take cancel the action, such that the protocol execution module pauses the countdown timer and removes the action from the individual patient monitoring devices such that the first confirmation no longer exists.

In a thirteenth aspect of the present disclosure, which may be combined with any other aspect listed herein unless specified otherwise, further comprising, prior to the countdown timer expiring, identifying an updated patient parameter with the individual patient monitoring device, determining that the updated patient parameter no longer violates the threshold, and removing the action from the selected protocol, such that the action is no longer displayed at the protocol execution module.

In a fourteenth aspect of the present disclosure, which may be combined with any other aspect listed herein unless specified otherwise, a protocol execution module includes a memory, one or more processors, in communication with the memory, where the protocol execution module is configured to display a plurality of protocols. The protocol execution module is further configured to receive, from a user, a selected protocol, the selected protocol associated with an individual medical therapy device being one of a plurality of medical therapy devices and associated with an individual patient monitoring device being one of a plurality of patient monitoring devices. The protocol execution module is further configured to identify a patient parameter with the individual patient monitoring device, and determine that the patient parameter violates a threshold. The threshold is dictated by the selected protocol. The individual medical therapy device takes an action, dictated by the selected protocol.

In a fifteenth aspect of the present disclosure, which may be combined with any other aspect listed herein unless specified otherwise, the individual medical therapy device is an infusion pump.

In a sixteenth aspect of the present disclosure, which may be combined with any other aspect listed herein unless specified otherwise, the action is one of increasing infusion rate of the infusion pump, decreasing infusion rate of the infusion pump, and ceasing infusion.

In a seventeenth aspect of the present disclosure, which may be combined with any other aspect listed herein unless specified otherwise, responsive to taking the action, the protocol execution module removes the selected protocol such that the selected protocol is no longer associated with the individual medical therapy device and the individual patient monitoring device.

In a eighteenth aspect of the present disclosure, which may be combined with any other aspect listed herein unless specified otherwise, a method includes displaying a plurality of protocols, and receiving a selected protocol, the selected protocol associated with an individual medical therapy device being one of a plurality of medical therapy devices and associated with an individual patient monitoring device being one of a plurality of patient monitoring devices. The individual medical therapy device receives, from the user, a first confirmation of the selected protocol. The protocol execution module receives, from the user, a second confirmation of the selected protocol. The protocol execution module executes the selected protocol with the individual medical therapy device.

In a nineteenth aspect of the present disclosure, which may be combined with any other aspect listed herein unless specified otherwise, the plurality of medical therapy devices includes at least one of an infusion pump, a dialysis or renal failure therapy machine, a respirator, and a defibrillators.

In a twentieth aspect of the present disclosure, which may be combined with any other aspect listed herein unless specified otherwise, the plurality of patient monitoring devices includes at least one of a heart rate sensor, a temperature sensor, a pulse oximetry sensor, a patient weight sensor, a glucose sensor, a respiratory sensor, a blood pressure sensor, a pressure sensor, and a volume-index sensor.

Additional features and advantages of the disclosed devices, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

Understanding that the figures depict only typical embodiments of the invention and are not to be considered to be limiting the scope of the present disclosure, the present disclosure is described and explained with additional specificity and detail through the use of the accompanying figures. The figures are listed below.

FIG. 7 is an illustration of a bedside brain interface while displaying a protocol summary with device configuration, according to an example embodiment of the present disclosure.

FIGS. 8 to 12 are illustrations of a bedside brain interface while displaying protocol settings, according to example embodiments of the present disclosure.

FIG. 23 is an illustration of a bedside brain central monitoring interface, according to an example embodiment of the present disclosure.

DETAILED DESCRIPTION OF EXAMPLE EMBODIMENTS

Figure 1:
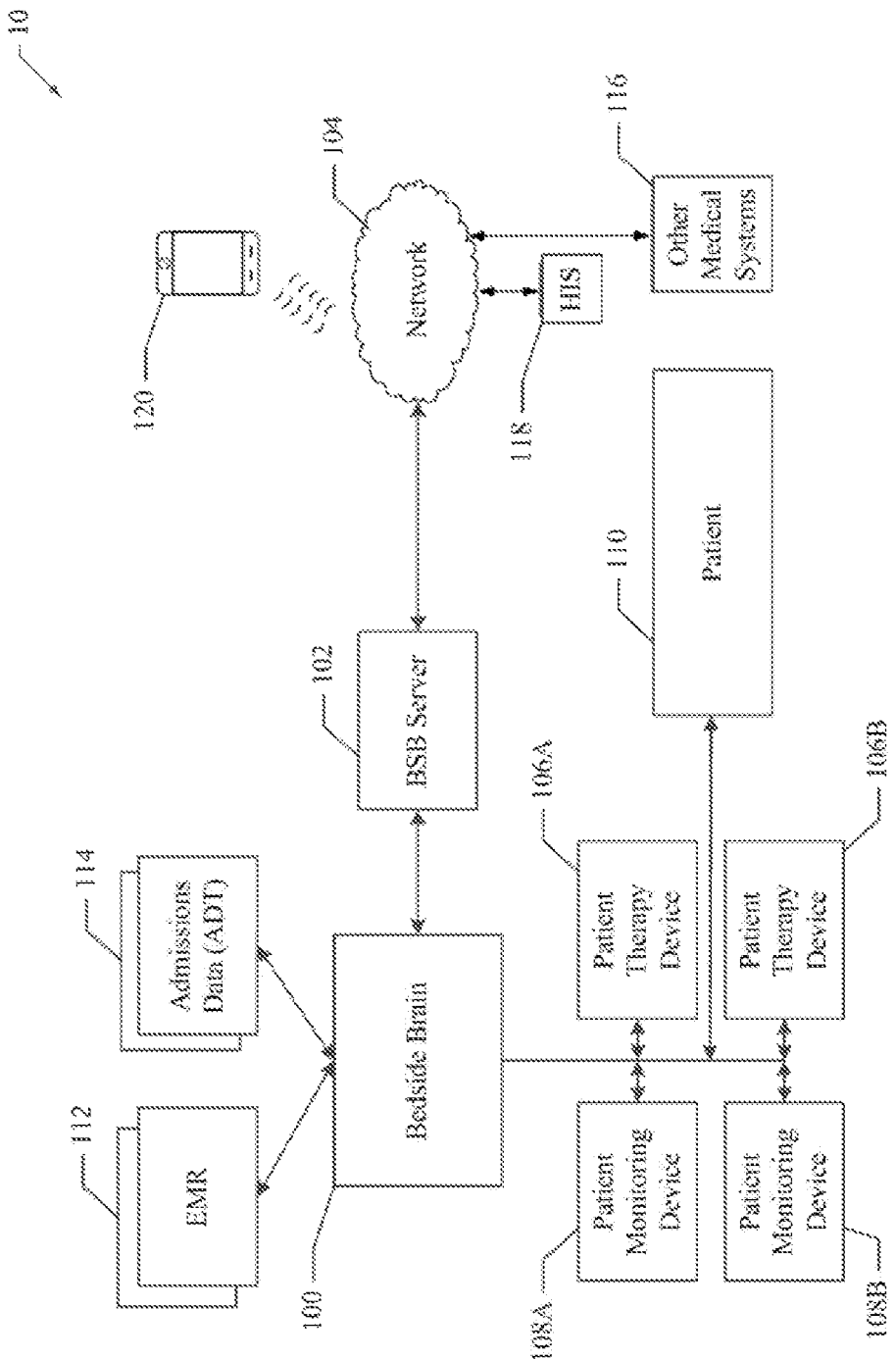
FIG. 1 is a system diagram of a hospital environment, including the bedside brain, according to an example embodiment of the present disclosure.

Referring to FIG. 1, a hospital environment 10 may include the bedside brain (also referred to herein as "BSB") 100. Bedside brain 100 includes a memory, such as a volatile or non-volatile memory device, such as RAM, ROM, EEPROM, or any other device capable of storing data. Bedside brain 100 further includes one or more processors, capable of executing instructions encoding arithmetic, logical, and/or I/O operations, in communication with the memory.

Bedside brain 100 may additionally include a bedside brain server 102, a cloud server or network 104, patient therapy devices 106A-B, and patient monitoring 108A-B. The patient therapy devices 106A-B and patient monitoring 108A-B are connected to a patient 110, such that the bedside brain 100 monitors and interacts with patient 110 via patient therapy devices 106A-B and patient monitoring 108A-B. The bedside brain 100 may communicate with additional external components, such as electronic medical records ("EMR") 112, admissions/discharge/transfer records 114, and other medical systems 116. It should be appreciated that communication between bedside brain 100 and external components can be wired communication or wireless communication, and may occur directly or indirectly, such as via bedside brain server 102 and/or network 104. For example, communication may include an Ethernet network, LAN, WLAN and/or in addition to an external network such as the Internet. The network 104 is communicatively coupled to a hospital information system ("HIS") 118, one or more additional medical networks, and/or one or more clinician devices 120. For example, bedside brain 100 may send status and patient information to external entities (e.g., caregivers, electronic medical records systems, mobile applications, etc.) and external devices (e.g., laptops, tablets, cellphones, etc.).

Regarding external systems, such as the EMR 112 and other similar external systems, these external systems may provide inputs to bedside brain 100, such as specific laboratory data, as required by some protocols (described in greater detail herein). The external systems may also provide patient specific information for individual protocols (e.g., patient age). The external systems may collect bedside brain 100 data, as required for patient management. Similarly, patient admission data, admission/discharge/transfer records 114, and related external systems (e.g., EMR 112) may be used, by the bedside brain 100, to provide for and verify patient identity and other patient information.

Regarding the bedside brain server 102, the bedside brain server 102 provides local management and gateway functions including, for example, gateway functions to the hospital network. The bedside brain server 102 provides information, as required by the bedside brain 100, such as specific rule protocols. The bedside brain server 102 monitors the status of multiple bedside brains, such as in a hospital network (e.g., connected to the server). The bedside brain server 102 collects data sent by the bedside brain 100 and provides analytic information (e.g., performance information, patient information, etc.). The bedside brain server 102 provides bedside brain management functions, such as firmware updates, device status monitoring, diagnostic and usage information, quality of service measures, etc.

Regarding the cloud server or network 104 (also referred to herein as simply "the cloud"), the cloud 104 may be a single server, a group of servers or, alternatively, may be distributed within a cloud computing framework, such that components of the bedside brain 100 may remotely access the cloud computing framework. The cloud 104 stores data for analysis by humans, and by machine learning systems, for new rule creation and identification. The cloud 104 provides rule specifications at the corporate level (e.g., standard rule specifications). The cloud 104 provides monitoring and analysis tools for bedside brain 100 worldwide, including global management and support of bedside brain 100, including firmware updates, etc. The cloud 104 provides the corporate repository for information collected by the bedside brain 100. The cloud 104 provides information for rule specification creation.

Patient therapy devices 106A-B may include infusion pumps, such as linear volume parenteral pumps, ambulatory infusion pumps, volumetric infusion pumps, or any other pump capable of delivering an intravenous therapy to the patient 110. Patient therapy devices 106A-B may likewise include dialysis or renal failure therapy machines, such as any hemodialysis, hemofiltration, hemodiafiltration, continuous renal replacement therapy ("CRRT"), or peritoneal dialysis ("PD") machines. Patient therapy devices 106A-B may likewise include respirators and defibrillators. Generally, patient therapy devices 106A-B may be any device configured to provide a therapy to patient 110. Therapy devices 106A-B may provide input on device state, or other inputs such as device monitored input parameters. For example, a defibrillator may provide ECG monitored input parameters.

Patient monitoring devices 108A-B may include any patient monitor and/or physiological sensor, such as a heart rate sensor (e.g., an EKG sensor and/or an ECG sensor), a temperature sensor, a pulse oximetry sensor, a patient weight scale, a glucose sensor, a respiratory sensor, a blood pressure sensor, a pressure sensor, or any other sensor for determining a physiological parameter or vital sign from patient 110 and/or display data regarding the patient 110 or treatment of the patient 110.

Bedside brain 10 may further include a patient monitor configured to display information, including information associated with patient therapy devices 106A-B and status information for patient therapy devices 106A-B, information associated with patient monitoring devices 108A-B and status information for patient monitoring devices 108A-B, and information associated with patient 110. This information may be displayed graphically for user readability. For example, the monitor of bedside brain 100 may display the data from various sensors via a time-based graph, via numerical values, via color coding, and/or via any other graphical means. The monitor may be wired or wirelessly coupled to the bedside brain 100. Going forward, for readability, it is assumed that bedside brain 100, in addition to processing and memory capabilities previously noted, includes the monitor. However, it should be noted that in certain embodiments bedside brain 100 does not require a monitor.

Bedside brain 100 may include input from additional sources, including a rule specification creator, an engineer or technician (e.g., for setup and configuration, periodic maintenance, firmware upgrades, etc.), an administrator, a clinician, or a patient.

Bedside brain 100 may include an operator interface (e.g., a touchscreen, a physical mouse/keyboard, etc.) to receive patient inputs (e.g., patient vitals) and other data (e.g., patient data from electronic medical records and other sources). This operator interface may also advantageously be used for rule creation, as detailed further herein.

Bedside Brain Protocols

Figure 2:
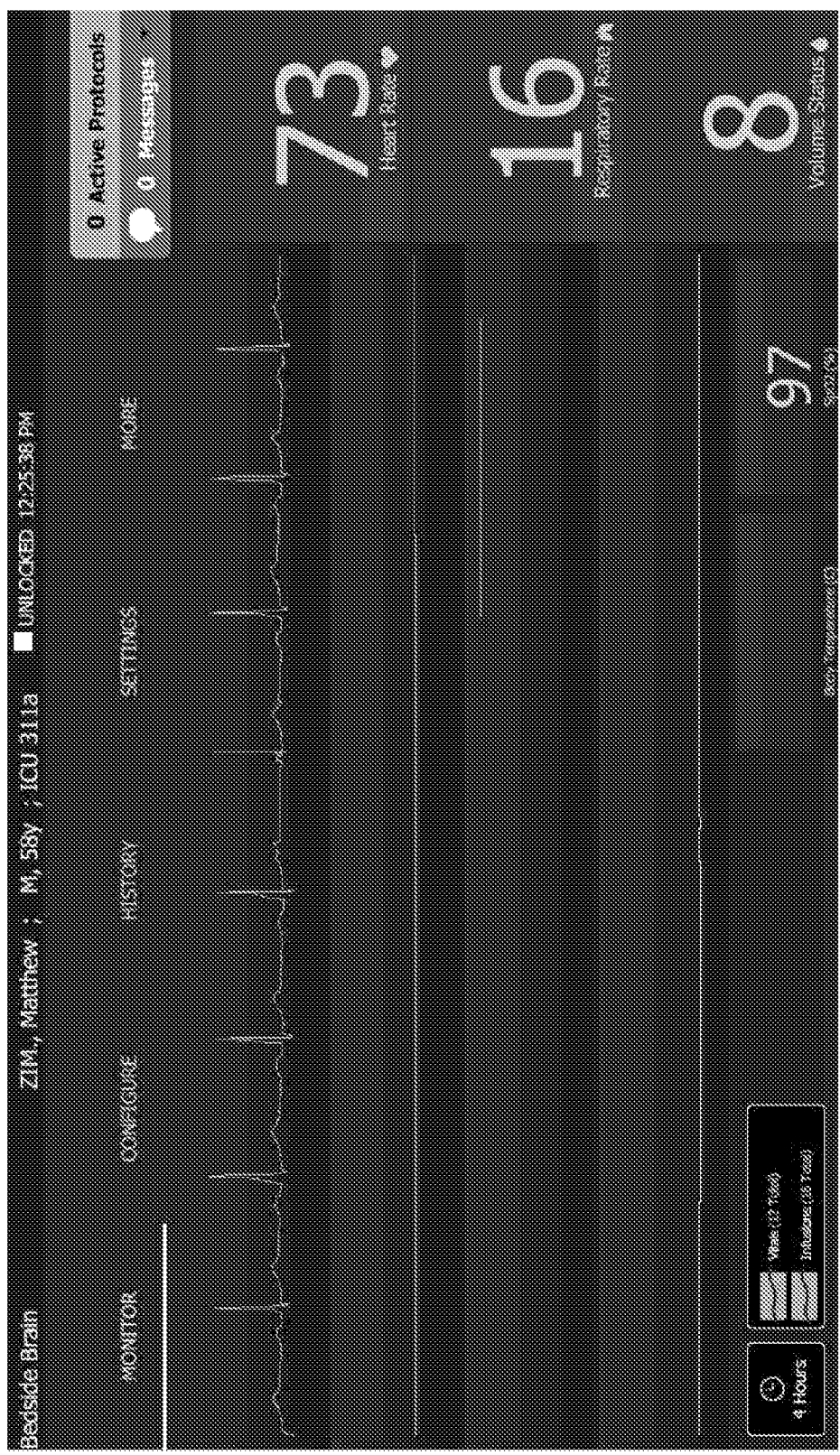
FIG. 2 is an illustration of a bedside brain interface indicating protocols and messages, according to an example embodiment of the present disclosure.

To comprehend the bedside brain 100, it is easiest to walk through its functionality with an example. FIG. 2 illustrates the interface of bedside brain 100. Specifically, bedside brain 100 indicates physiological parameters of patient 110, as measured by patient monitoring devices 108A-B. For example, the heart rate, the respiratory rate, and the volume status of the patient are displayed. Each of these physiological parameters is displayed both numerically and graphically. It should be appreciated that any number of patient monitoring devices 108A-B can be used, to measure any number of physiological parameters of patient 110. Bedside brain 100 indicates that there are zero active safety protocols (also referred to herein generally as "protocols") and that there are zero messages.

Figure 3:
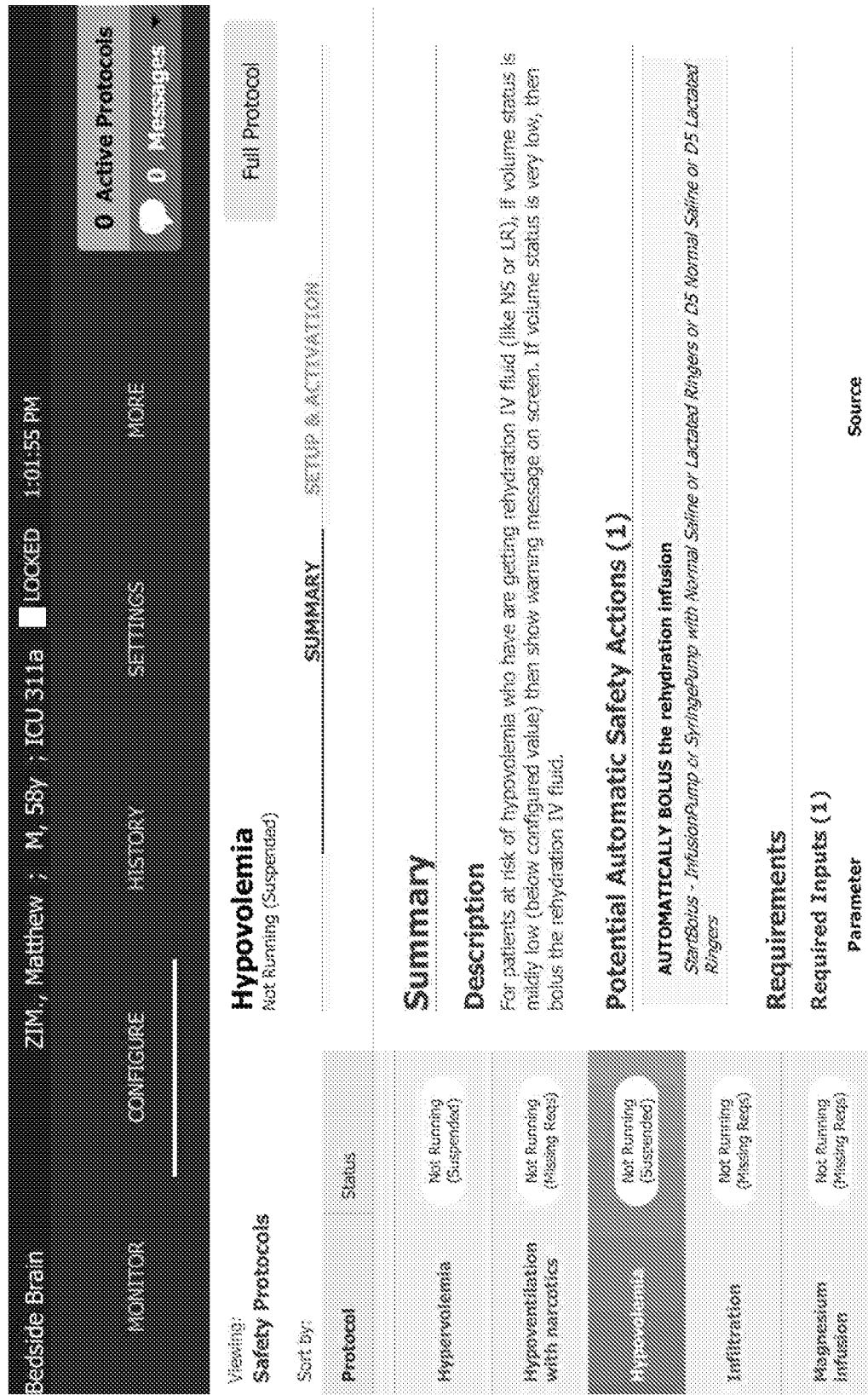
FIG. 3 is an illustration of a bedside brain interface while configuring protocols, according to an example embodiment of the present disclosure.

FIG. 3 illustrates the interface of bedside brain 100, while configuring protocols. More specifically, a user, such as a nurse, doctor, or other healthcare provider, has selected "Configure." By selecting "Configure," the user is able to view all protocols that the bedside brain 100 is capable of running.

Bedside brain 100 is only capable of running protocols that it is aware of (e.g., bedside brain 100 must have stored the rule syntax for the particular protocol). Furthermore, bedside brain 100 is only capable of running protocols for connected patient therapy devices 106A-B and connected patient monitoring devices 108A-B. For example, bedside brain 100 may require that at least one of the connected patient monitoring devices 108A-B is an ECG monitor, if the protocol requires that bedside brain 100 identify heart rate. Likewise, for example, bedside brain 100 may require that at least one of the connected patient therapy devices 106A-B is an infusion pump, if the protocol action requires the bedside brain 100 to cease patient infusion. If all required system parameters are fulfilled (e.g., patient monitoring device parameters, patient therapy device parameters, etc.), the protocol will be identified in a protocol list by bedside brain 100. Thus, bedside brain 100 provides a listing of only protocols that the bedside brain 100 is capable of running with a given system. Bedside brain 100 also identifies if any capable protocols are currently running. In the example illustrated in FIG. 2, none of the capable protocols are running.

If the user selects a particular protocol, such as "Hypovolemia," bedside brain 100 displays a summary of the protocol. For example, bedside brain 100 displays a description of the protocol, including what typical patient parameters may trigger action by bedside brain 100. Bedside brain also displays any "Potential Automatic Safety Actions." These are actions that bedside brain 100 could potentially take, if there is no intervention by the user once certain conditions are met. Likewise, bedside brain 100 may display required inputs. For example, the "Hypovolemia" protocol requires volume index for patient 110 (e.g., a unitless number identifying the volume status of patient 110).

Figure 4:
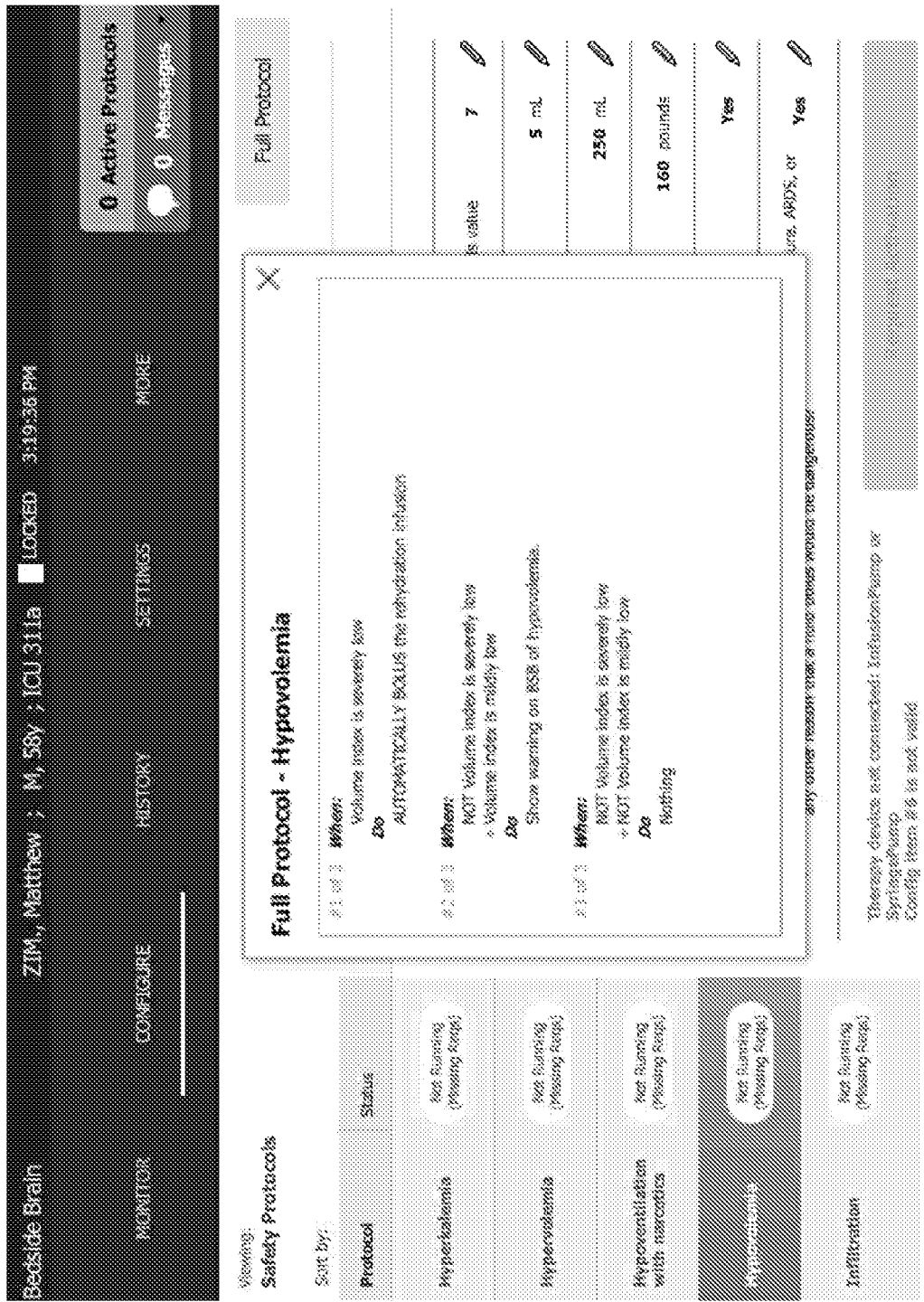
FIG. 4 is an illustration of a bedside brain interface while displaying a complete protocol logic, according to an example embodiment of the present disclosure.

Bedside brain 100 also offers the user with the ability to select "Full Protocol." FIG. 4 illustrates the interface of bedside brain 100, while displaying a complete protocol logic for the "Hypovolemia" protocol. Namely, bedside brain 100 identifies the entire logical flow of the protocol, including each possible logical determination and the related action that is taken by bedside brain 100 (e.g., "When: Volume index is severely low" . . . "AUTOMATICALLY BOLUS the rehydration infusion", etc.). This "Full Protocol" display is useful, as it distills a complex decision tree of if-then statements into a user-readable format. Specifically, each individual logical determination and related action is listed in plain-text, including logical determinations that result in no action (e.g., "Do: Nothing"). This complete protocol logic is beneficial to users who are non-technical.

Figure 5:
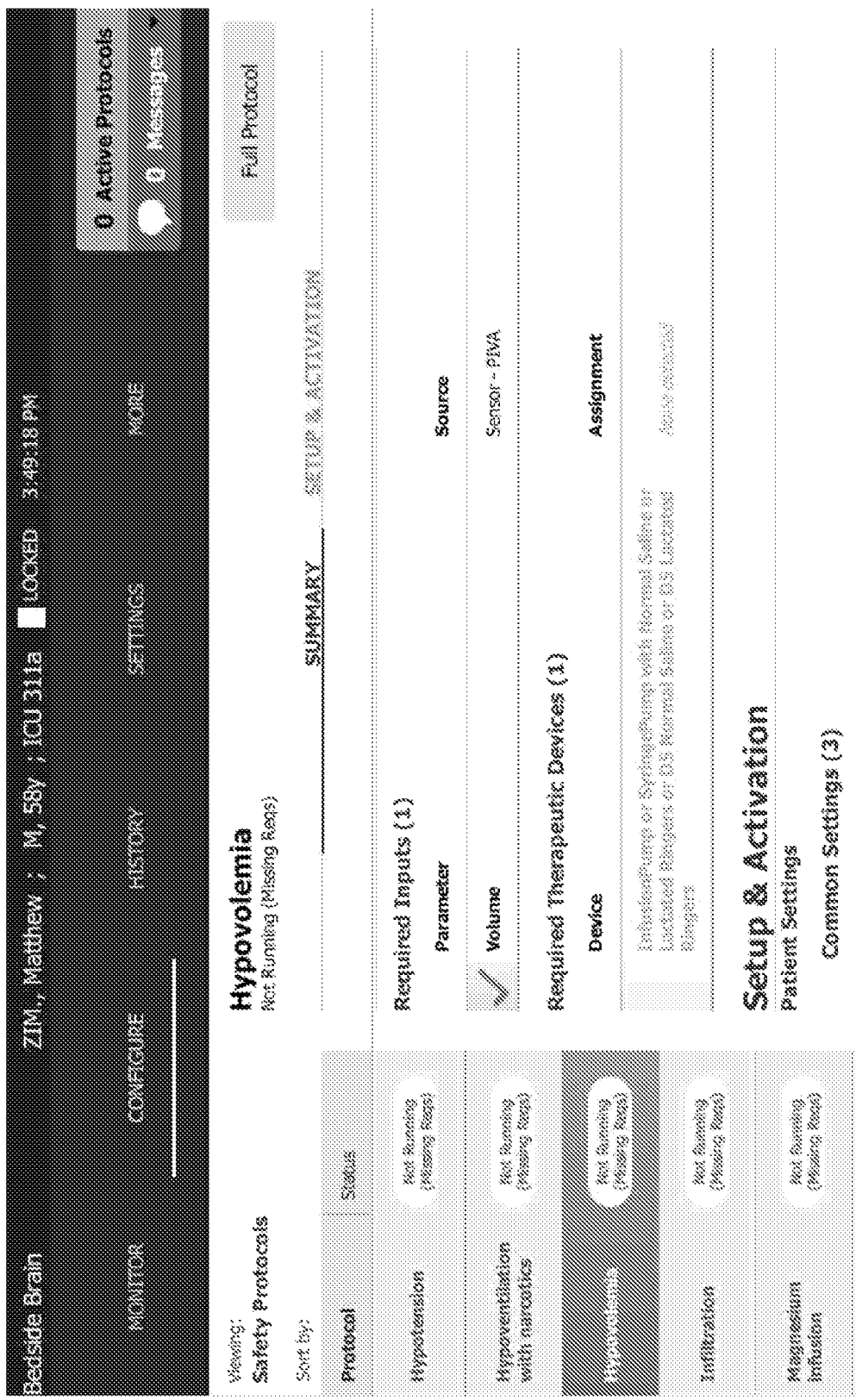
FIG. 5 is an illustration of a bedside brain interface while displaying a protocol summary, according to an example embodiment of the present disclosure.

FIG. 5 illustrates the interface of bedside brain 100, while displaying the protocol summary once selected. As noted previously, bedside brain 100 may display required inputs. For example, the "Hypovolemia" protocol may require volume index for patient 110 (e.g., the unitless number identifying the volume status of patient 110). Bedside brain 100 may further display required devices, such as patient therapy devices 106A-B and/or patient monitoring devices 108A-B. With the "Hypovolemia" protocol, bedside brain requires an infusion pump or syringe pump, with either saline or lactated ringers as the delivered therapy. Bedside brain 100 also indicates that the required therapy device is not detected (e.g., "None detected"). Bedside brain 100 will not active the "Hypovolemia" protocol, until the required device is detected and configured appropriately.

Figure 6A:
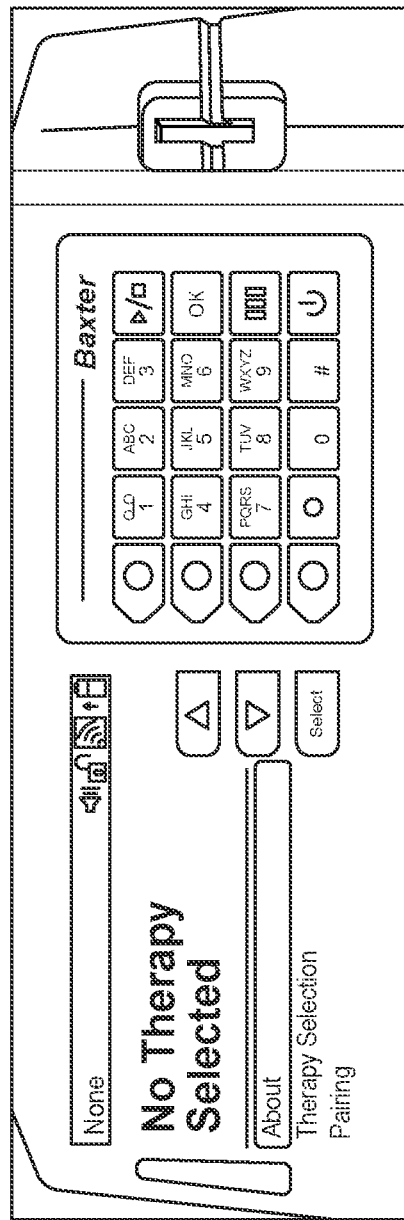
FIGS. 6A to 6D are illustrations of a therapy device interface during configuration, according to example embodiments of the present disclosure.
Figure 6B:
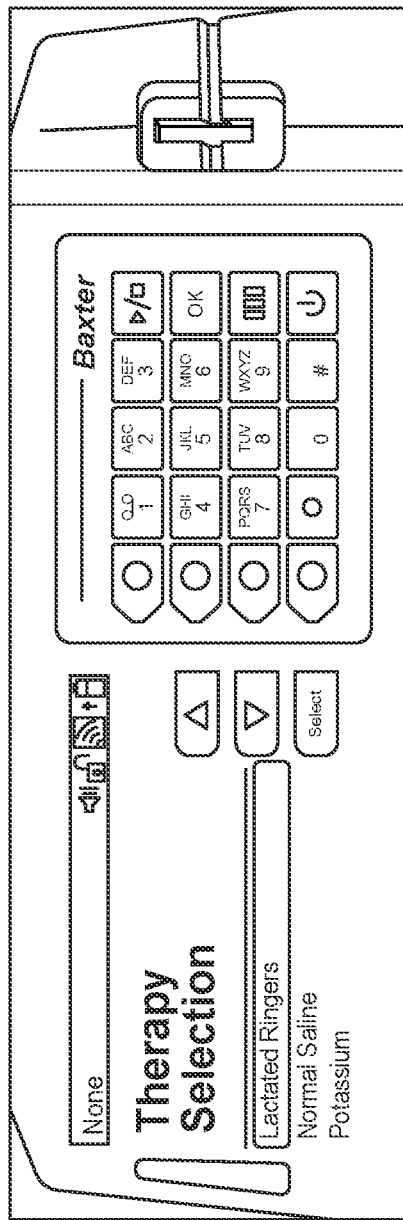
Figure 6C:
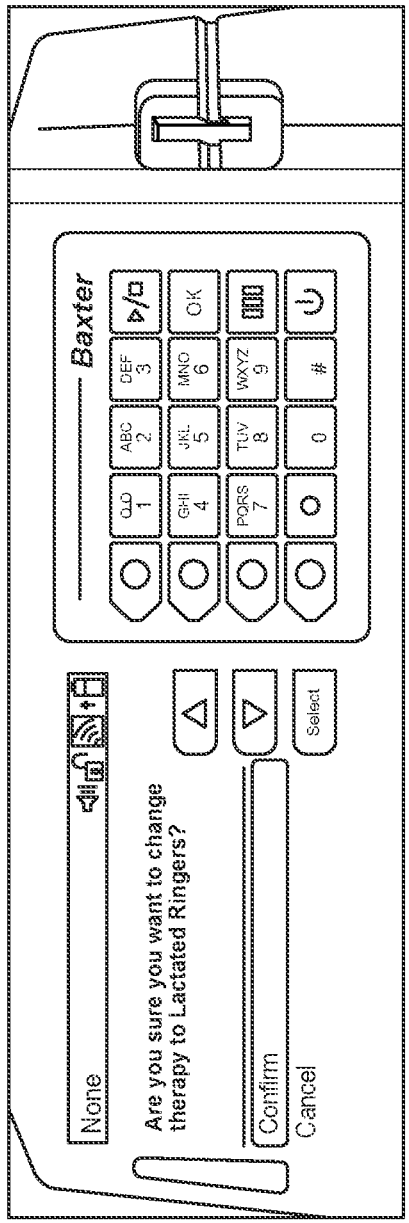
Figure 6D:
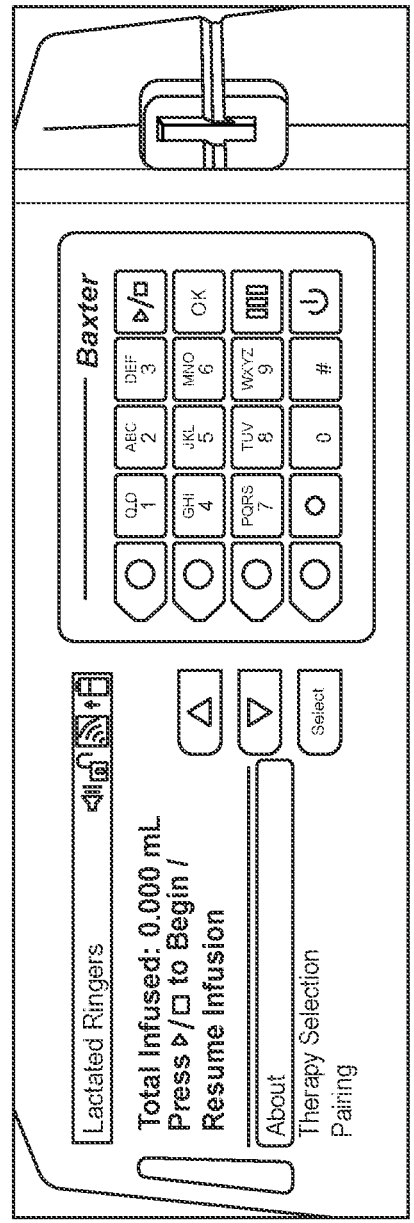

FIGS. 6A to 6D illustrate an individual therapy device interface during configuration. Specifically, FIG. 6A illustrates patient therapy device 106A, which is an infusion pump. As indicated on the display of the patient therapy device 106A, "No Therapy" has been selected by the user. FIG. 6B illustrates that a "Lactated Ringers" infusion therapy has been selected by the user. FIG. 6C illustrates patient therapy device 106A, requiring the user to confirm the selected infusion therapy. Once confirmed, FIG. 6D illustrates that the patient therapy device 106A is configured for the selected infusion therapy: "Lactated Ringers" infusion therapy.

Figure 7:
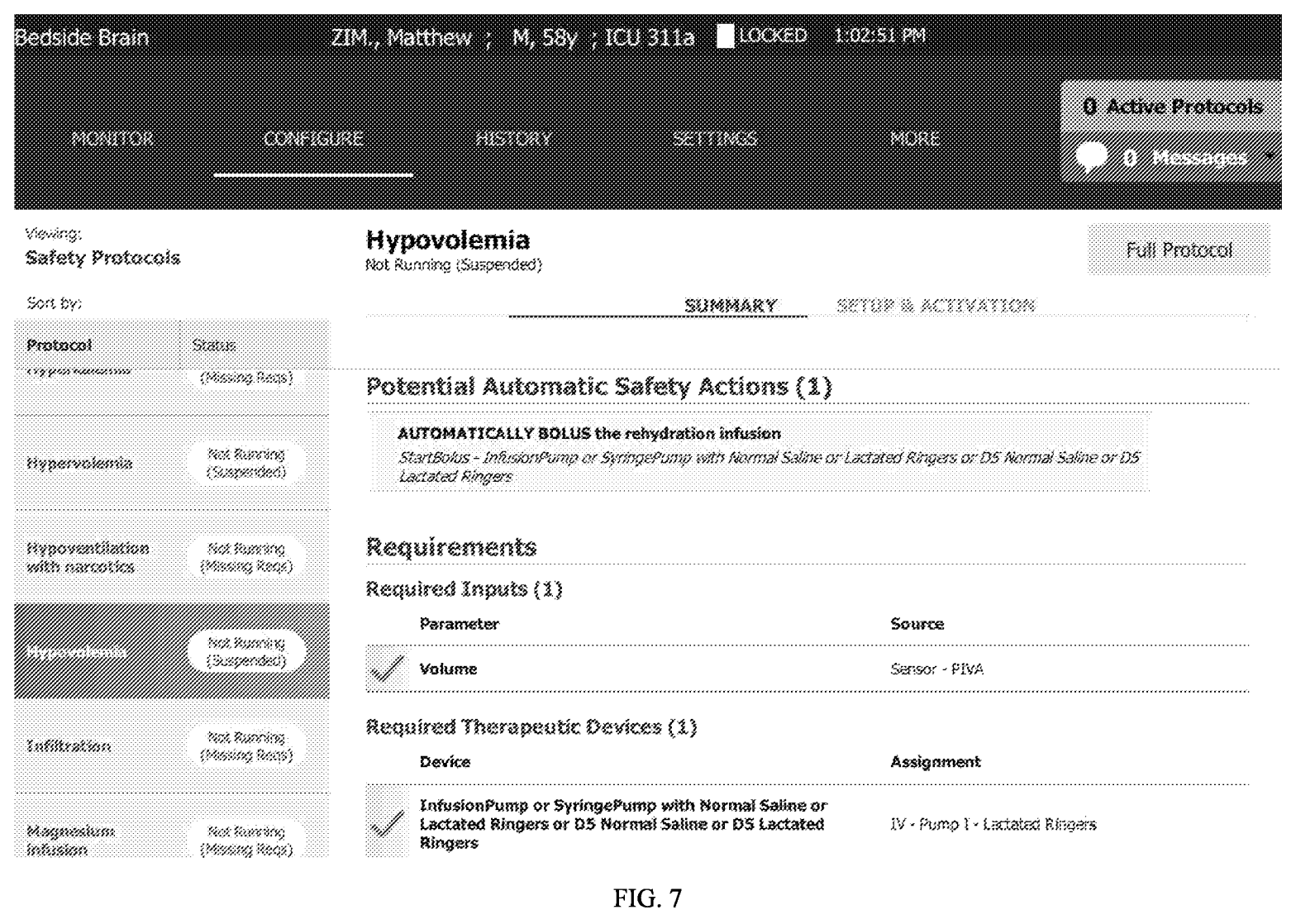

Returning to bedside brain 100, FIG. 7 illustrates the interface of bedside brain 100, while displaying the protocol summary with device configuration. Namely, while in FIG. 5 bedside brain 100 indicated that the required device was not detected (e.g., "None detected"), FIG. 7 illustrates that the required therapeutic device has been configured (e.g., an infusion pump with lactated ringers infusion per FIGS. 6A to 6D).

Figure 8:
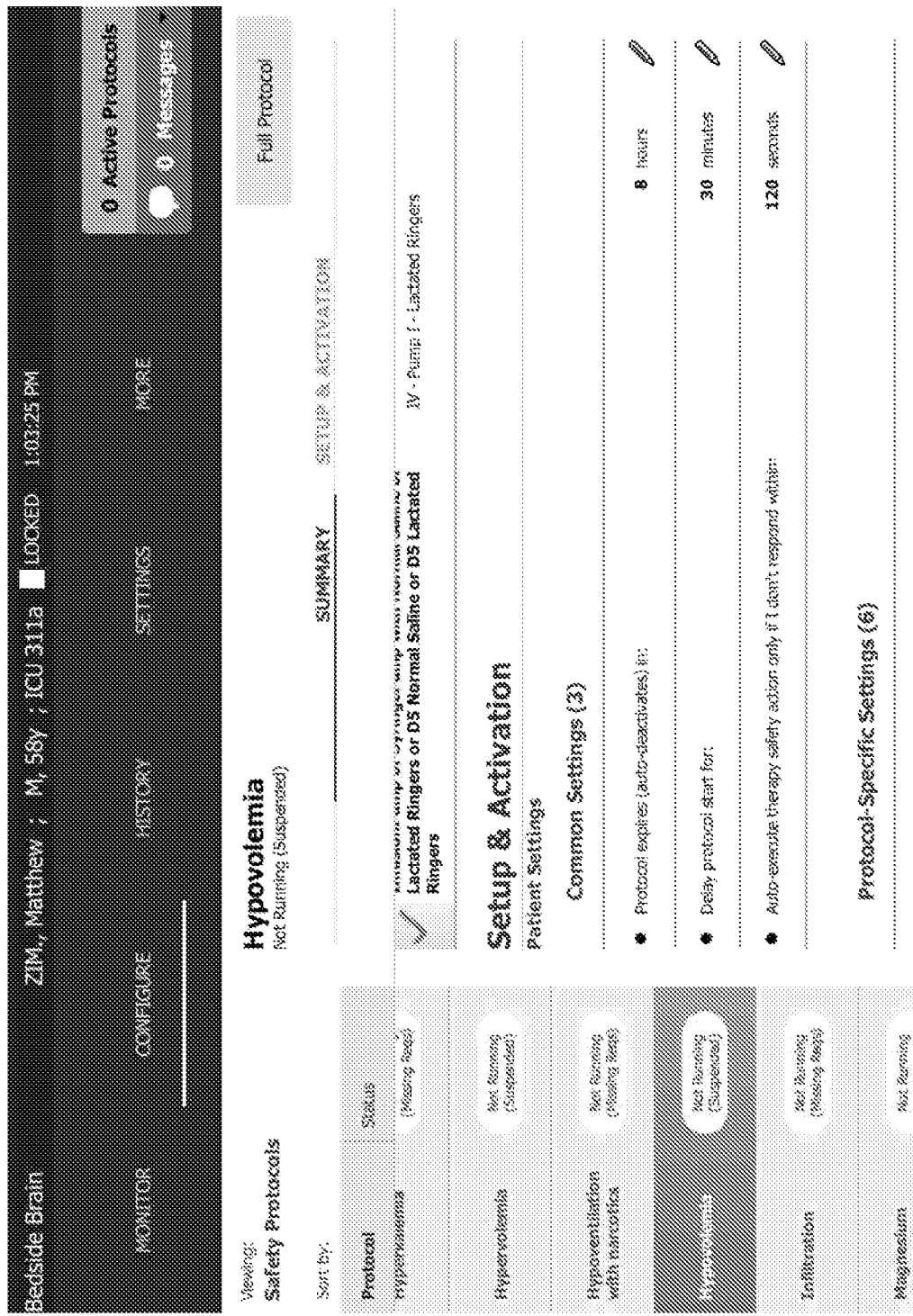

FIGS. 8 to 12 illustrate the interface of bedside brain 100, while displaying protocol settings. For example, FIG. 8 illustrates "Setup & Activation" for the particular protocol. Settings may include both common settings and protocol-specific settings. For example, common settings may include protocol expiry (e.g., when the protocol is automatically deactivated by bedside brain 100), protocol delay (e.g., if the user wants bedside brain 100 to wait a particular time before initiating the protocol), and auto-execute time (e.g., how long bedside brain 100 should wait, for the user to respond, before automatically taking an action). For example, regarding protocol expiry, the user can let the protocol run for as long as the patient 110 is in the hospital, or set it to automatically turn itself off after a certain amount of time (e.g., 8 hours).

Figure 9:
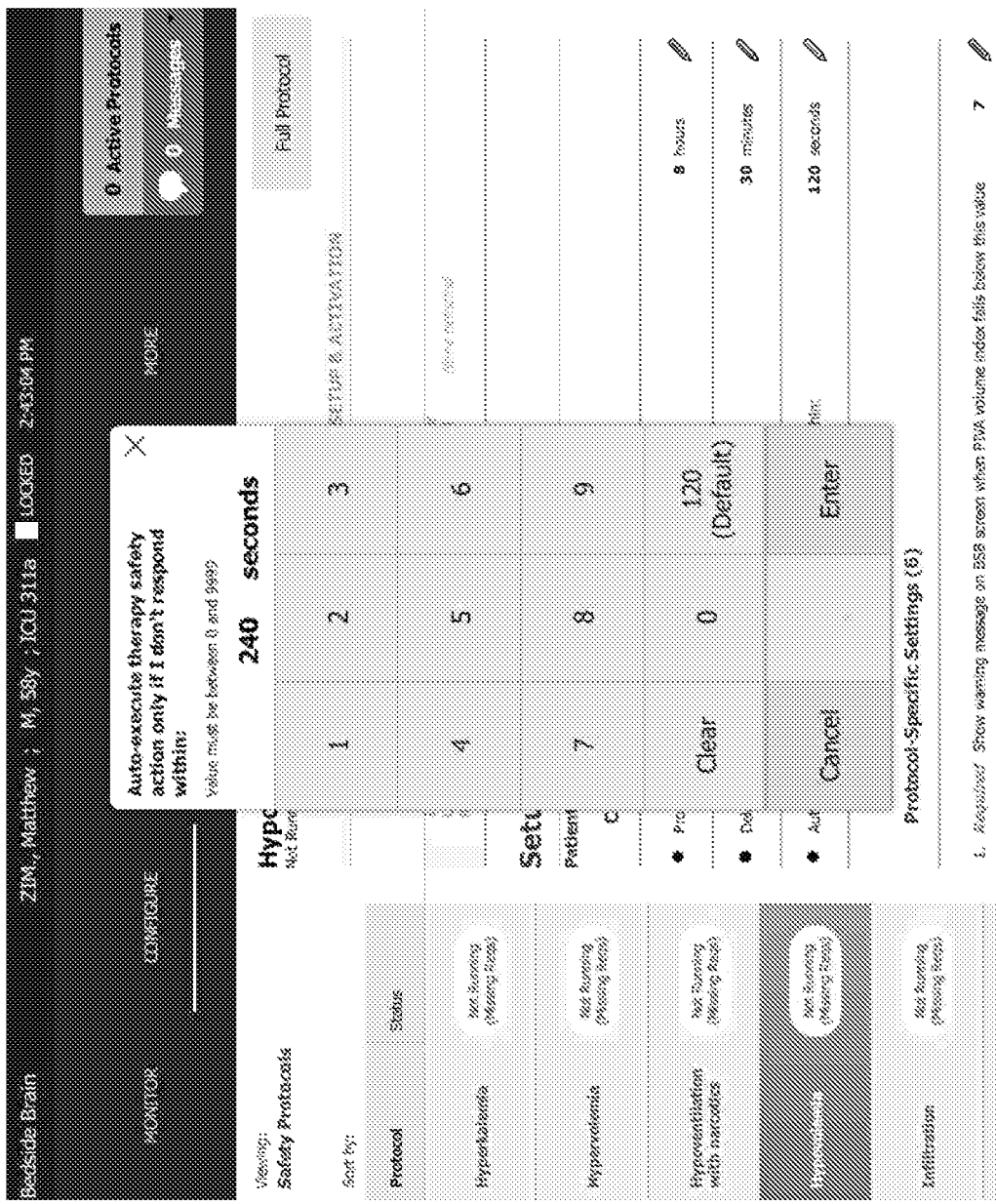

The user can update each of these common settings. For example, FIG. 9 illustrates the user selecting the common setting of auto-execute time. Bedside brain 100 displays a keyboard, such that the user can enter any time as desired (or may select the default time) directly into bedside brain 100. Bedside brain 100 further includes hard limits on the auto-execute time that can be entered by the user, ensuring that the entered range remains reasonable for a given protocol.

Figure 10:
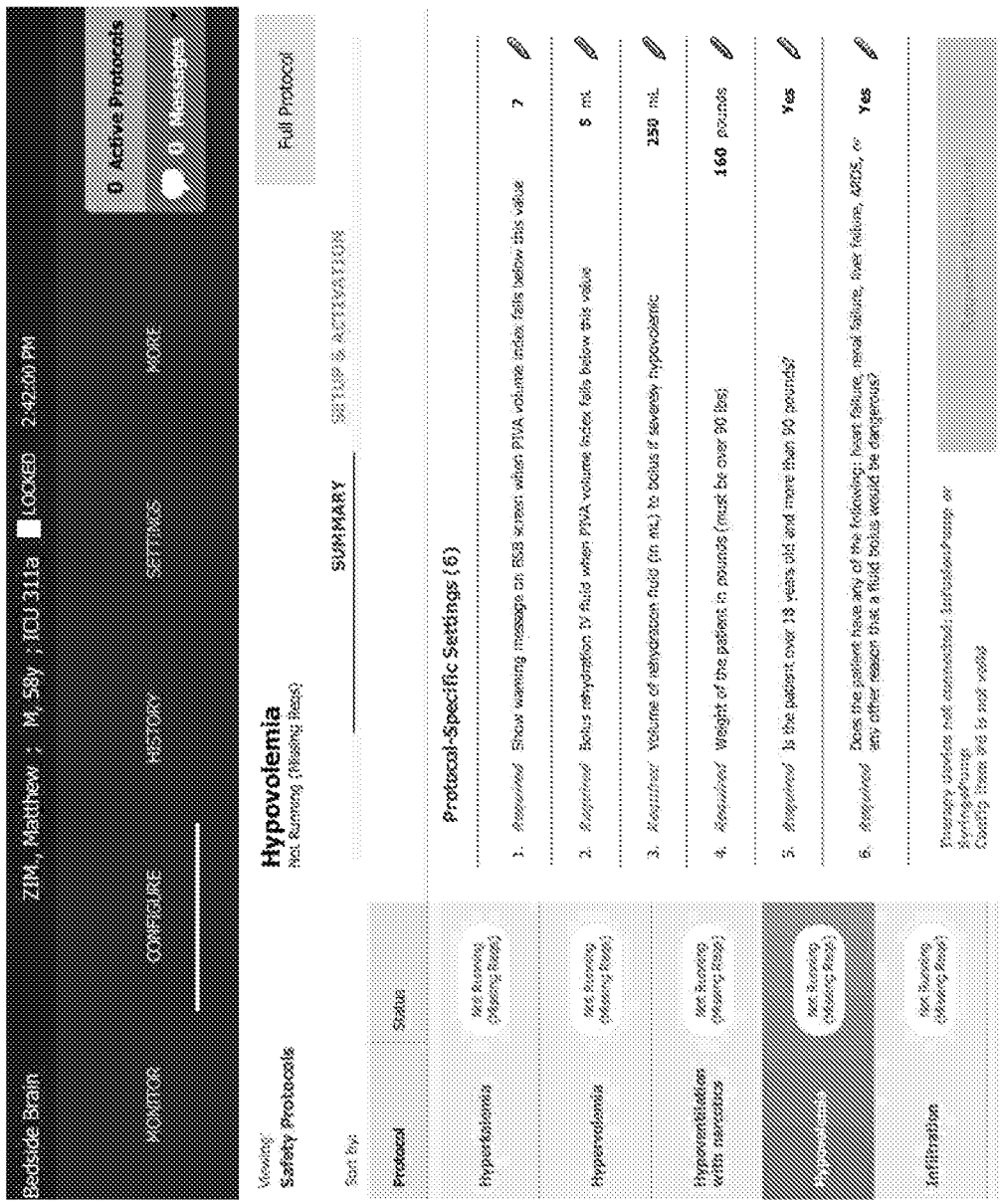
Figure 11:
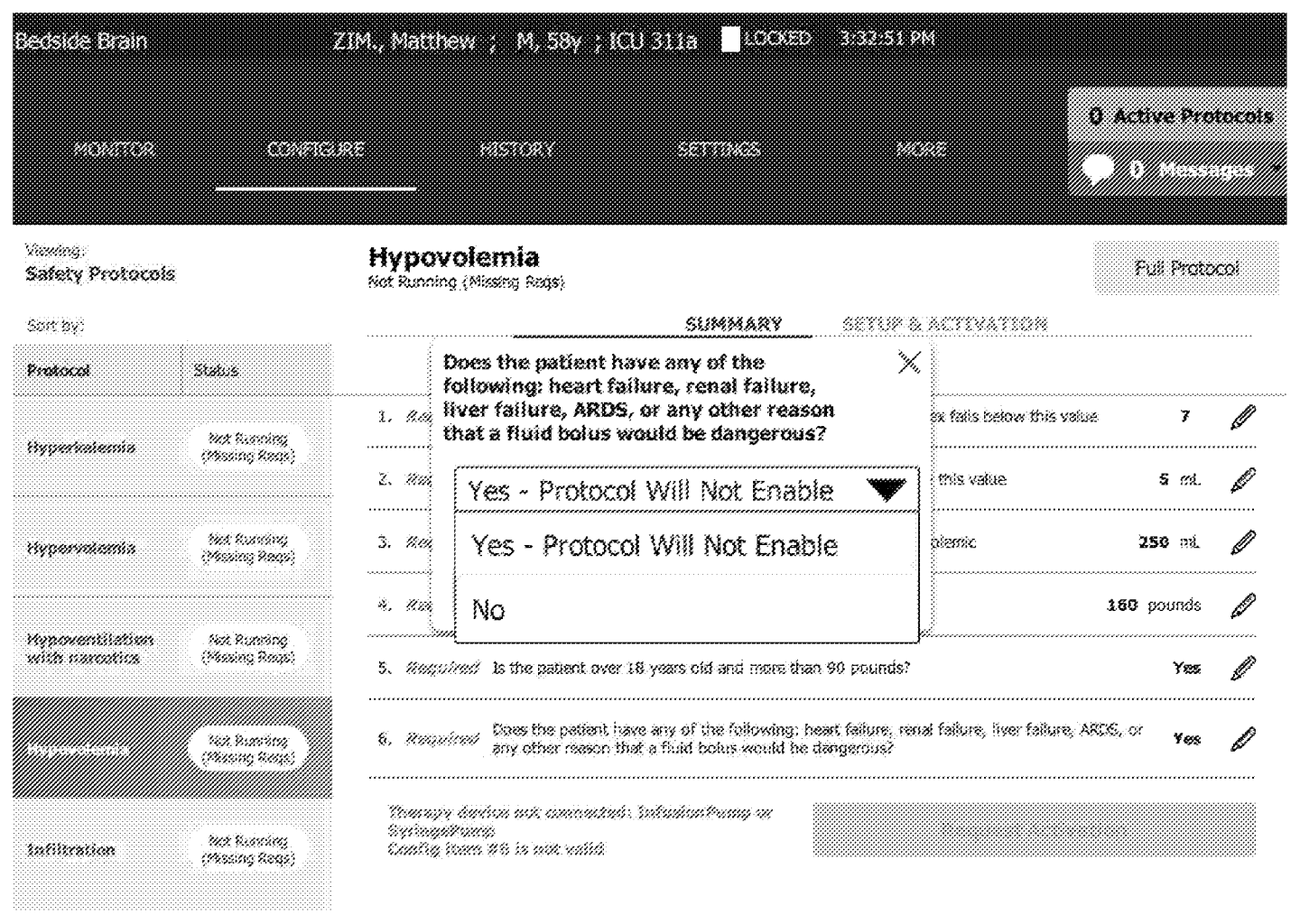

The user can also update the protocol-specific settings. For example, FIG. 10 illustrates the interface of bedside brain 100 indicating various protocol-specific settings. Specifically, with the "Hypovolemia" protocol, protocol-specific settings can include setting the level (e.g., volume index for patient 110) to show a warning message on bedside brain 100, setting the bolus value (e.g., 5 mL for rehydration), setting the rehydration value (e.g., 250 mL if severe dehydration is detected), setting the weight of the patient 110 (e.g., 140 lbs), setting the age of the patient, and setting any specific physiological conditions of the patient 110. Specifically, for example, FIG. 11 illustrates the interface of bedside brain 100 when the user has selected the specific physiological conditions (e.g., "Does the patient have any of the following [conditions]?"). It should be noted that various protocol-specific settings are required (as indicated by FIG. 10). For example, if the patient has "renal failure" bedside brain 100 will not enable the protocol. Thus, through protocol-specific settings, bedside brain 100 ensures that it is only used for ideal patients; patients that might have abnormal or unpredictable physiological results, or may be at risk for additional complications, are screened out at this stage.

Figure 12:
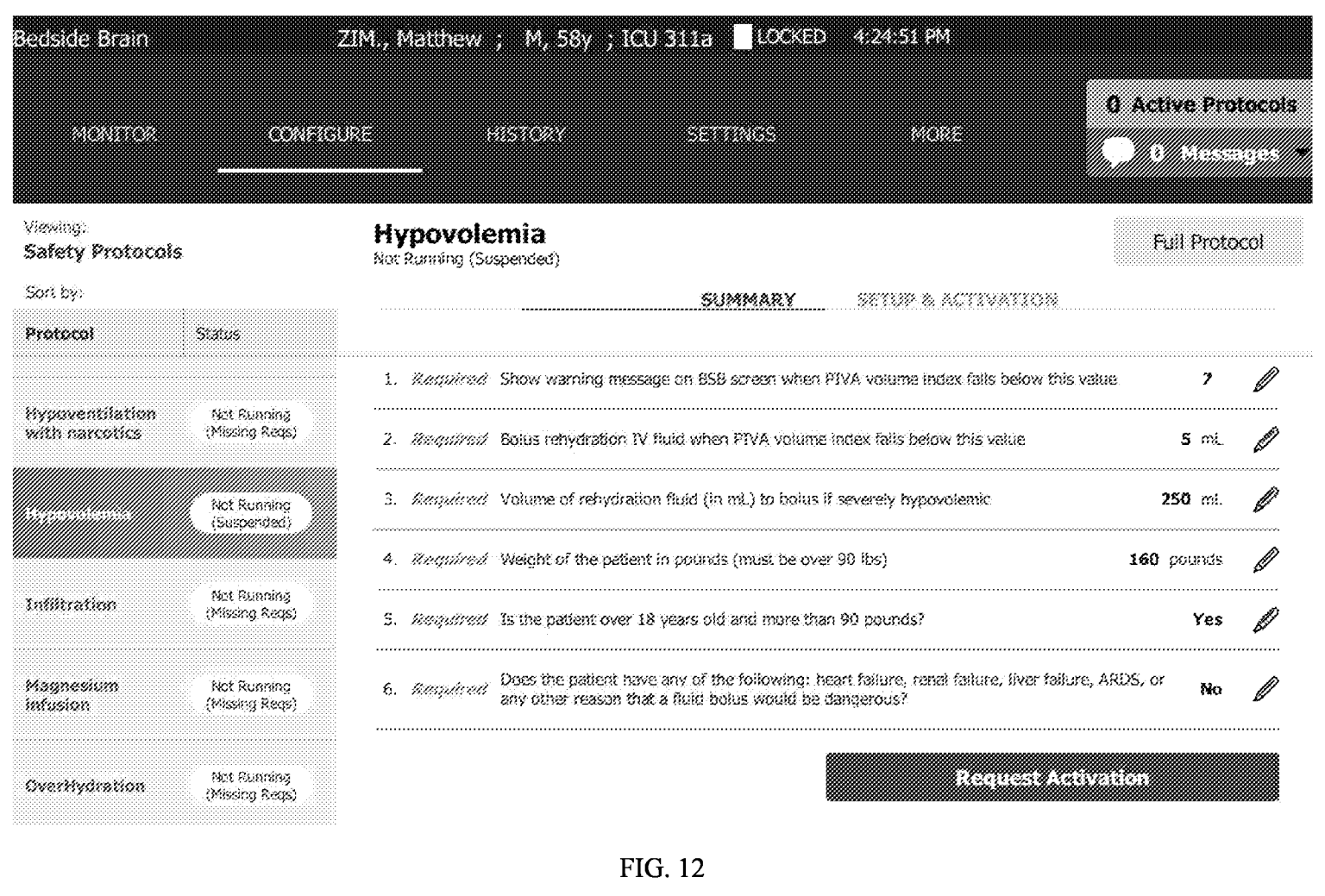

FIG. 12 illustrates the interface of bedside brain 100 once all protocol-specific settings have been entered by the user. Once all protocol-specific settings are entered, the "Request Activation" button appears on bedside brain 100. Upon selection, bedside brain additionally requires pre-approval on the device.

Figure 13:
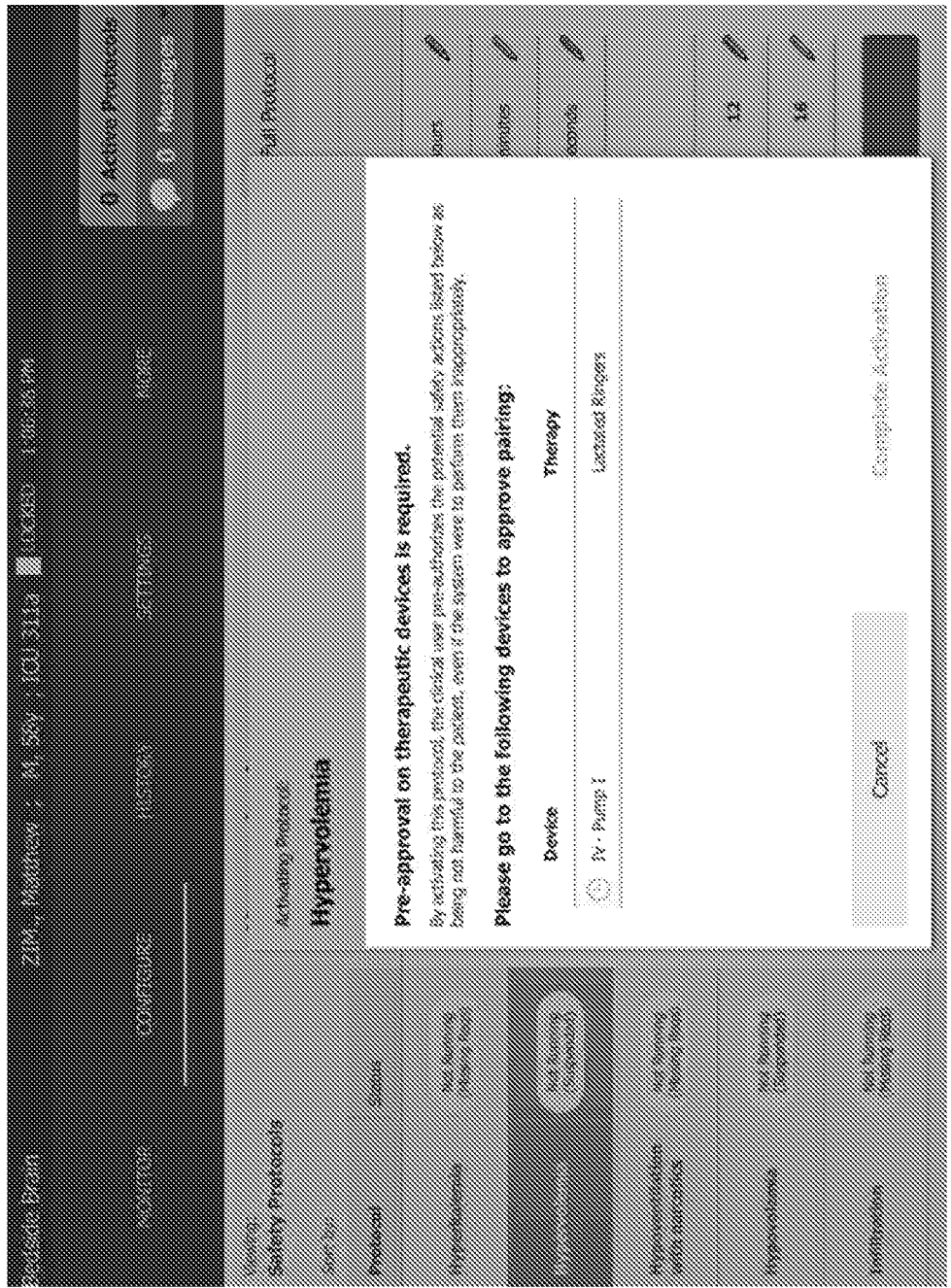
FIG. 13 is an illustration of a bedside brain interface requiring pre-approval, according to an example embodiment of the present disclosure.

For example, FIG. 13 illustrates the interface of bedside brain 100, requiring pre-approval on patient therapy device 106A. With pre-approval, bedside brain 100 identifies, to the user, the specific device on which the protocol will run (e.g., infusion pump) and the specific therapy with which the protocol will run (e.g., lactated ringers). Bedside brain 100 instructs the user to physically authorize the patient therapy device 106A by pairing it with bedside brain 100.

Figure 14:
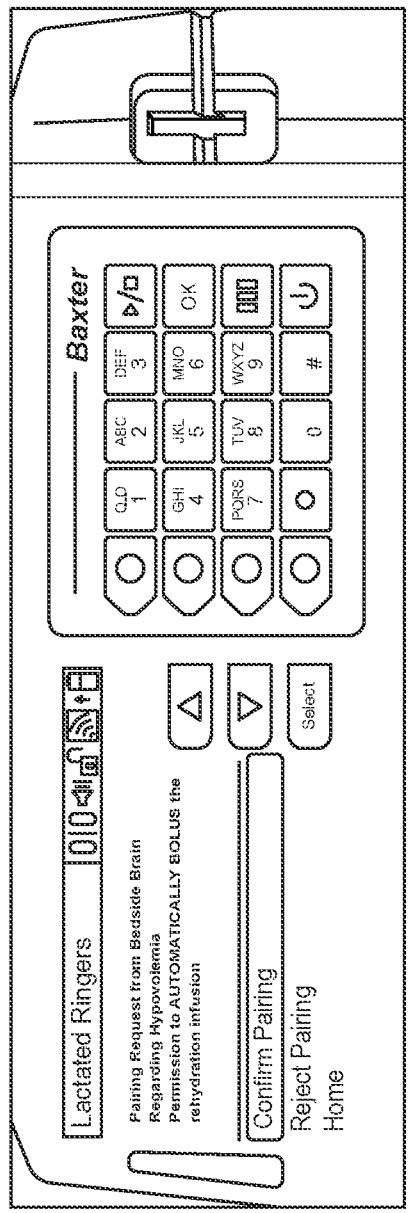
FIG. 14 is an illustration of a therapy device interface requiring pre-approval, according to an example embodiment of the present disclosure.

FIG. 14 illustrates the patient therapy device 106A at this stage. Specifically, the patient therapy device 106A displays the action of the protocol from bedside brain 100 (e.g., "Permission to AUTOMATICALLY BOLUS the rehydration infusion"). In this way, the user can both mentally and physically verify that the selected protocol from bedside brain 100 will be operating in tandem with this specific patient therapy device 106A. The patient therapy device 106A requires that the user physically confirm pairing with bedside brain 100, and pairing must be confirmed on the device 106A itself. Once pairing is confirmed, bedside brain 100 indicates that pre-approval has occurred.

Figure 15:
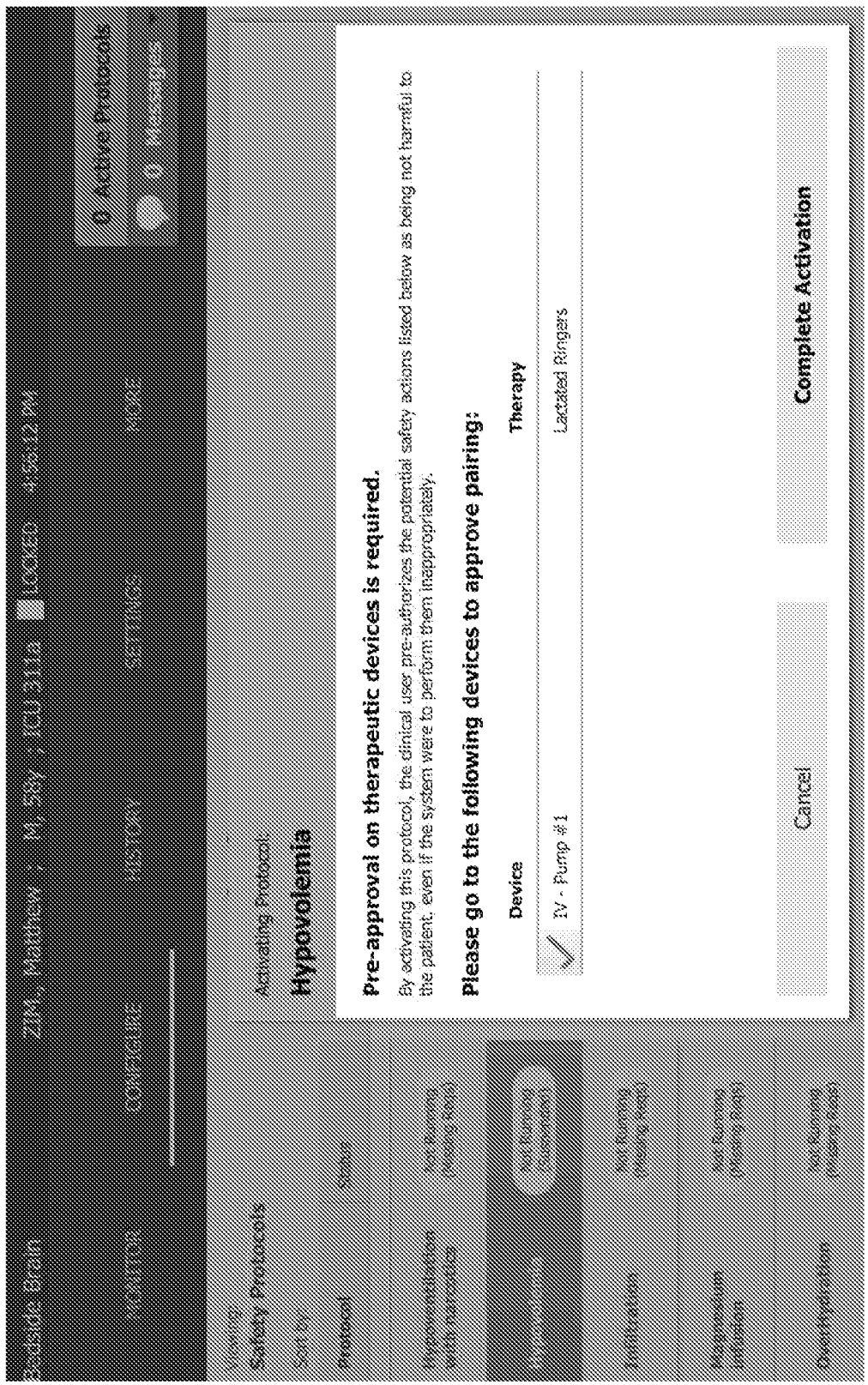
FIG. 15 is an illustration of a bedside brain interface confirming pre-approval, according to an example embodiment of the present disclosure.

Specifically, FIG. 15 illustrates the interface of bedside brain 100, indicating that patient therapy device 106A has been pre-approved (e.g., via the pairing process discussed above with respect to FIG. 14). The user can then choose to "Complete Activation" on bedside brain 100. In this way, the user is required to physically select the protocol, and configure the protocol, on bedside brain 100, then physically confirm the protocol on the patient therapy device 106A, then physically confirm the protocol on bedside brain 100. It is expected that this paradigm may ensure proper protocol configuration, reducing user error.

The process of device pre-approval, described above with reference to FIGS. 13 to 15 may be commonly referred to herein as "handshaking." In various embodiments, patient therapy devices 106A-B may include a wired input/output port, which may provide a physical communications connection to/from the bedside brain 100. In other embodiments, the patient therapy devices 106A-B and bedside brain 100 may communicate wirelessly, as supported by enterprise network rules (e.g., WPA2, EAP, RADIUS, etc.).

Generally, patient therapy devices 106A-B will not follow any commands (e.g., from the bedside brain 100) for taking therapeutic actions that have not been pre-approved on that specific device by the user. In an embodiment, patient therapy devices 106A-B will not follow any commands for therapeutic actions unless a protocol ID that accompanies the command from bedside brain 100 matches a protocol ID that was provided in a pre-approval workflow. In an embodiment, patient therapy devices 106A-B will not follow any commands for therapeutic actions unless the specific therapy in the command matches the specific therapy that was sent by the bedside brain 100 and pre-approved by the user in the pre-approval workflow. In an embodiment, patient therapy devices 106A-B will automatically expire the pre-approval, and no longer follow any commands for therapeutic actions from the bedside brain 100, after a pre-approval expiration time has passed.

Figure 16:
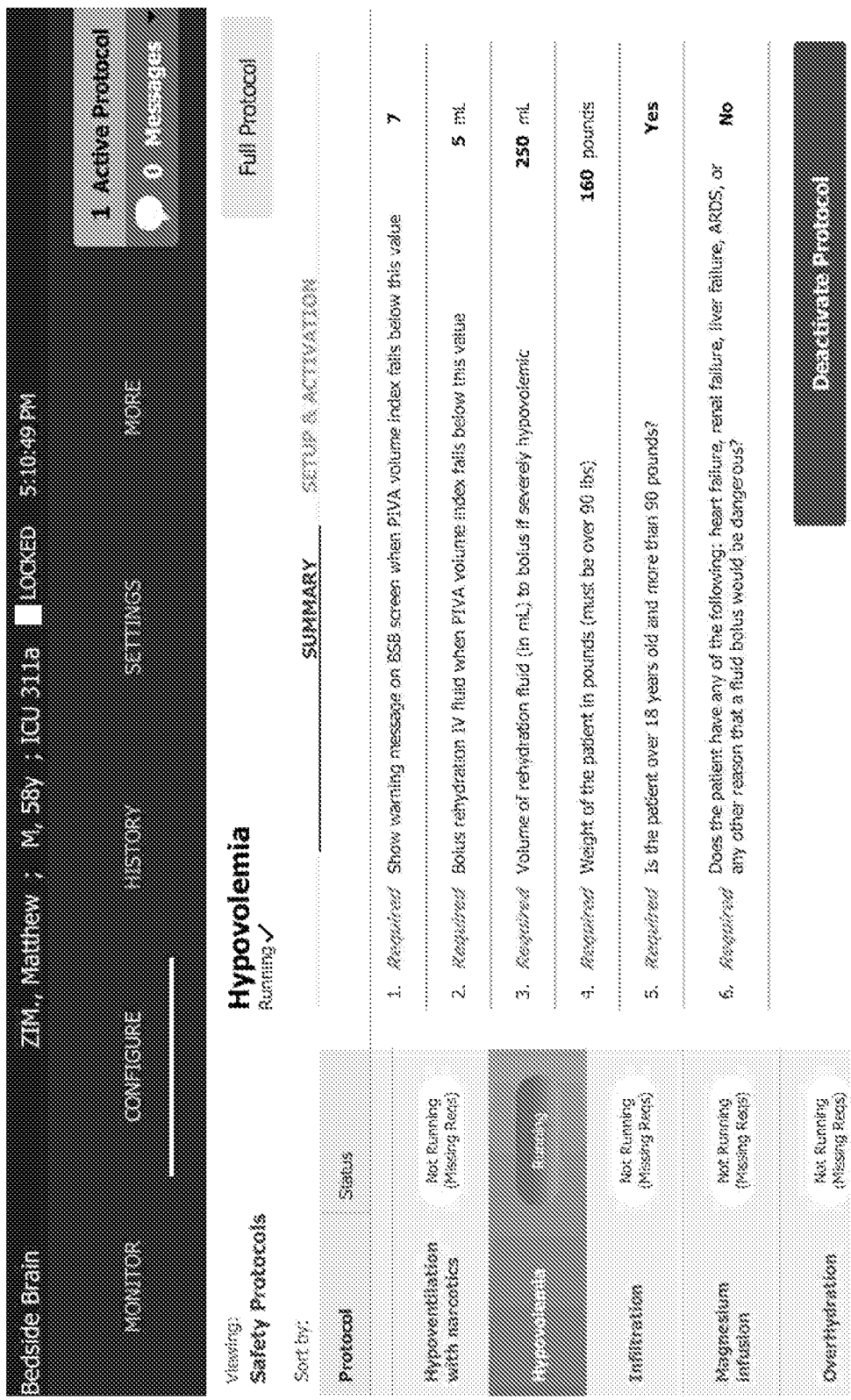
FIG. 16 is an illustration of a bedside brain interface displaying a protocol summary while running, according to an example embodiment of the present disclosure.

FIG. 16 illustrates the interface of bedside brain 100, indicating the Hypovolemia protocol is now running. For example, bedside brain 100 indicates the specific Hypovolemia protocol as "Running" in the protocol listing. Likewise, bedside brain 100 indicates that there is an active protocol in the status window next to messages.

Figure 17:
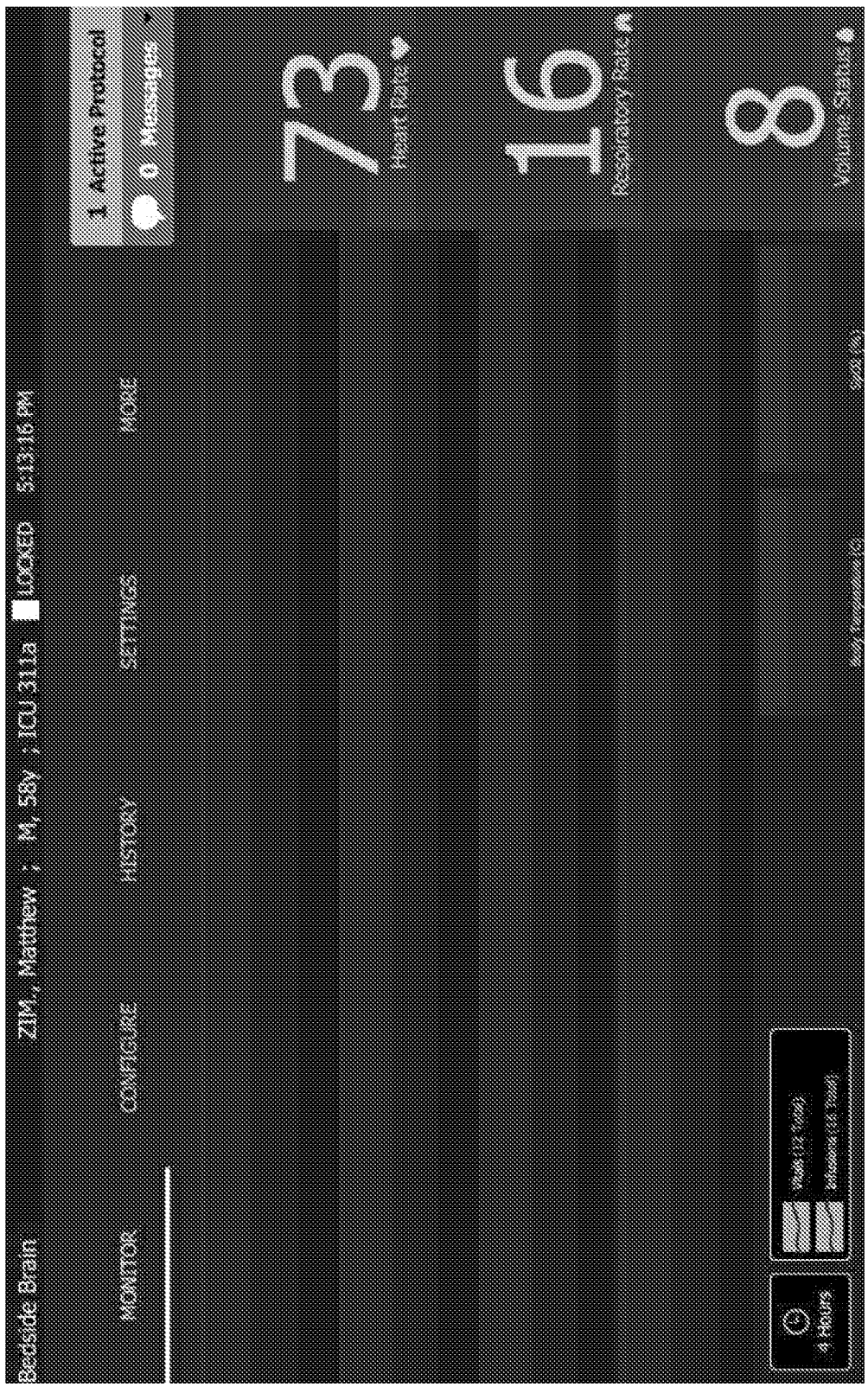
FIG. 17 is an illustration of a bedside brain interface indicating protocols and messages while a protocol is running, according to an example embodiment of the present disclosure.

FIG. 17 illustrates the interface of bedside brain 100, similar to the interface previously illustrated by FIG. 2. However, FIG. 17 indicates that there is one active protocol. Though the protocol is active, patient parameters including the heart rate, the respiratory rate, and the volume status of the patient 110, as obtained by patient monitoring devices 108A-B, are well within the ranges dictated by the protocol settings. Bedside brain 100 monitors patient physiological parameters and may either store this information locally (e.g., on internal memory) or remotely (e.g., on server 102 and/or network 104). Bedside brain 100 may additionally synchronize data or send changes in patient physiological parameters and/or treatment parameters to the EMR 112. At a later point in time, the patient 100 may experience a deteriorating condition, such that his physiological parameters change in undesirable ways.

Figure 18:
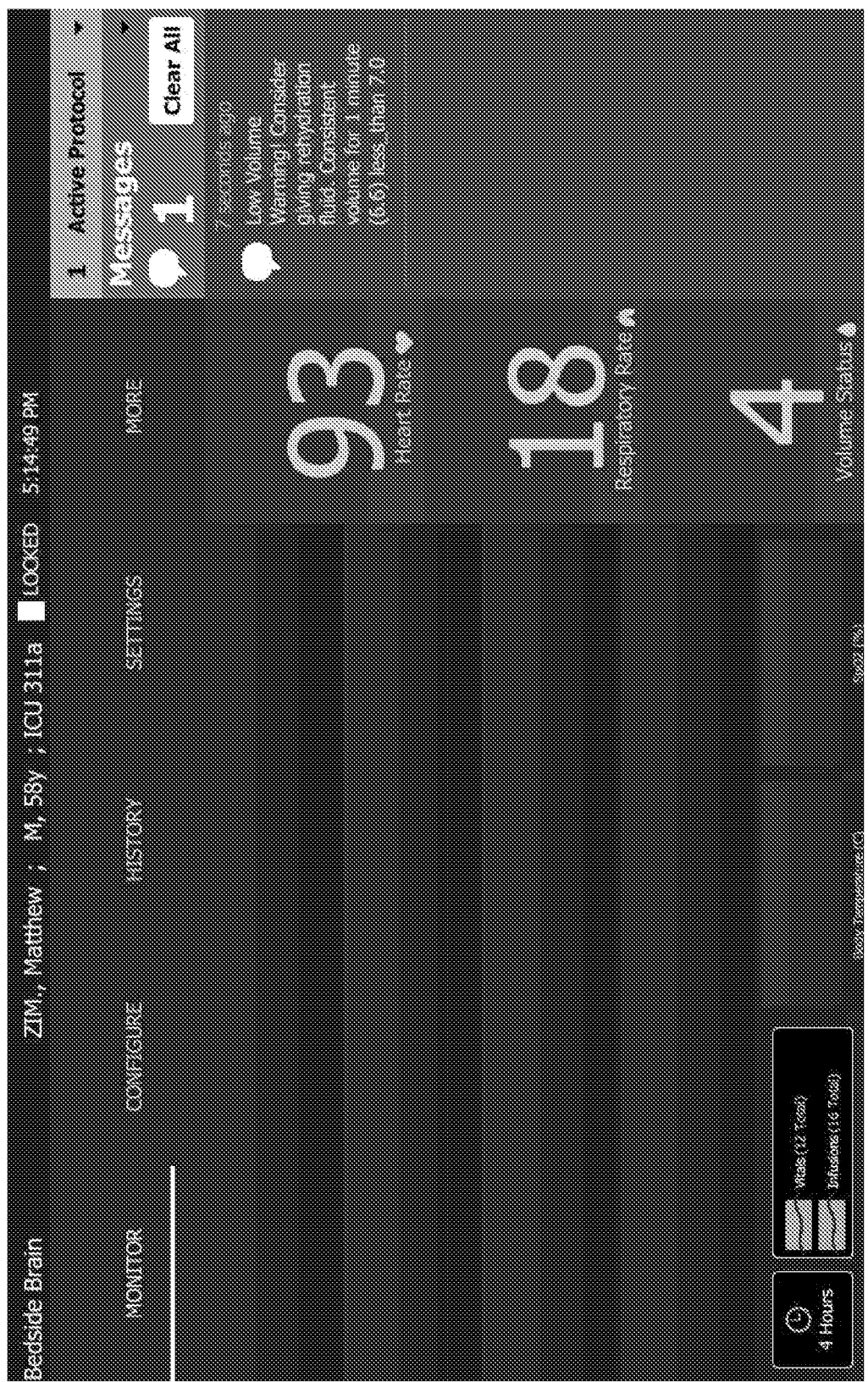
FIG. 18 is an illustration of a bedside brain interface displaying a message while a protocol is running, according to an example embodiment of the present disclosure.

For example, when compared to FIG. 17, FIG. 18 illustrates the interface of bedside brain 100 where the volume index for patient 110 (e.g., a unitless number identifying the volume status of patient 110) has dropped from 8 (a satisfactory value per the "Hypovolemia" protocol) to 4 (an unsatisfactory value per the "Hypovolemia" protocol). According to the protocol-specific settings (e.g., described with respect to FIGS. 4 and 12 above), bedside brain 100 will show a warning message if volume index goes below 7. Thus, as illustrated in FIG. 18, bedside brain 100 displays the warning message. Bedside brain 100 additionally provides the user with a recommended course of action in response to the patient condition triggering the warning message (e.g., low volume status).

Figure 19:
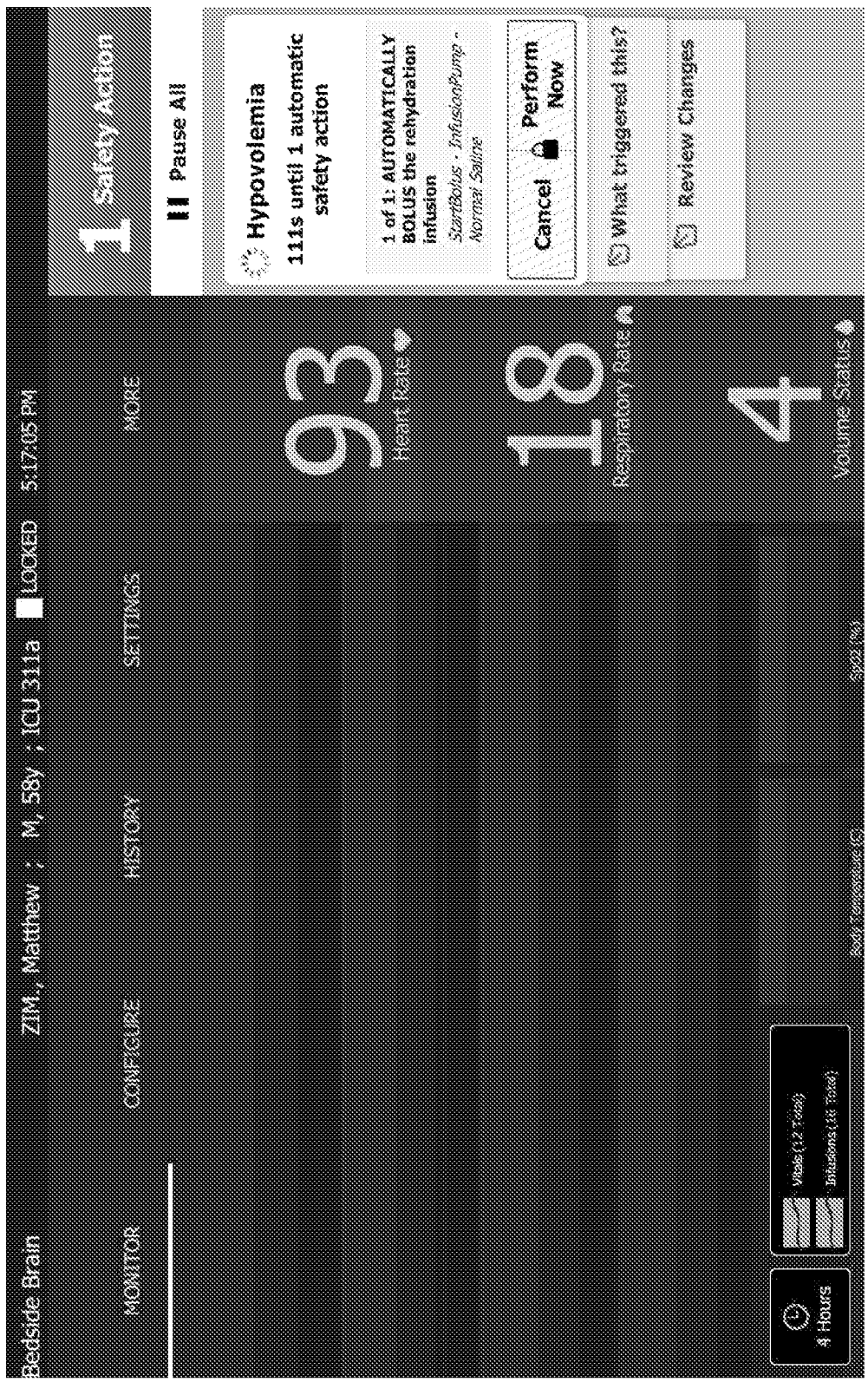
FIG. 19 is an illustration of a bedside brain interface displaying a safety action while a protocol is running, according to an example embodiment of the present disclosure.
Figure 20:
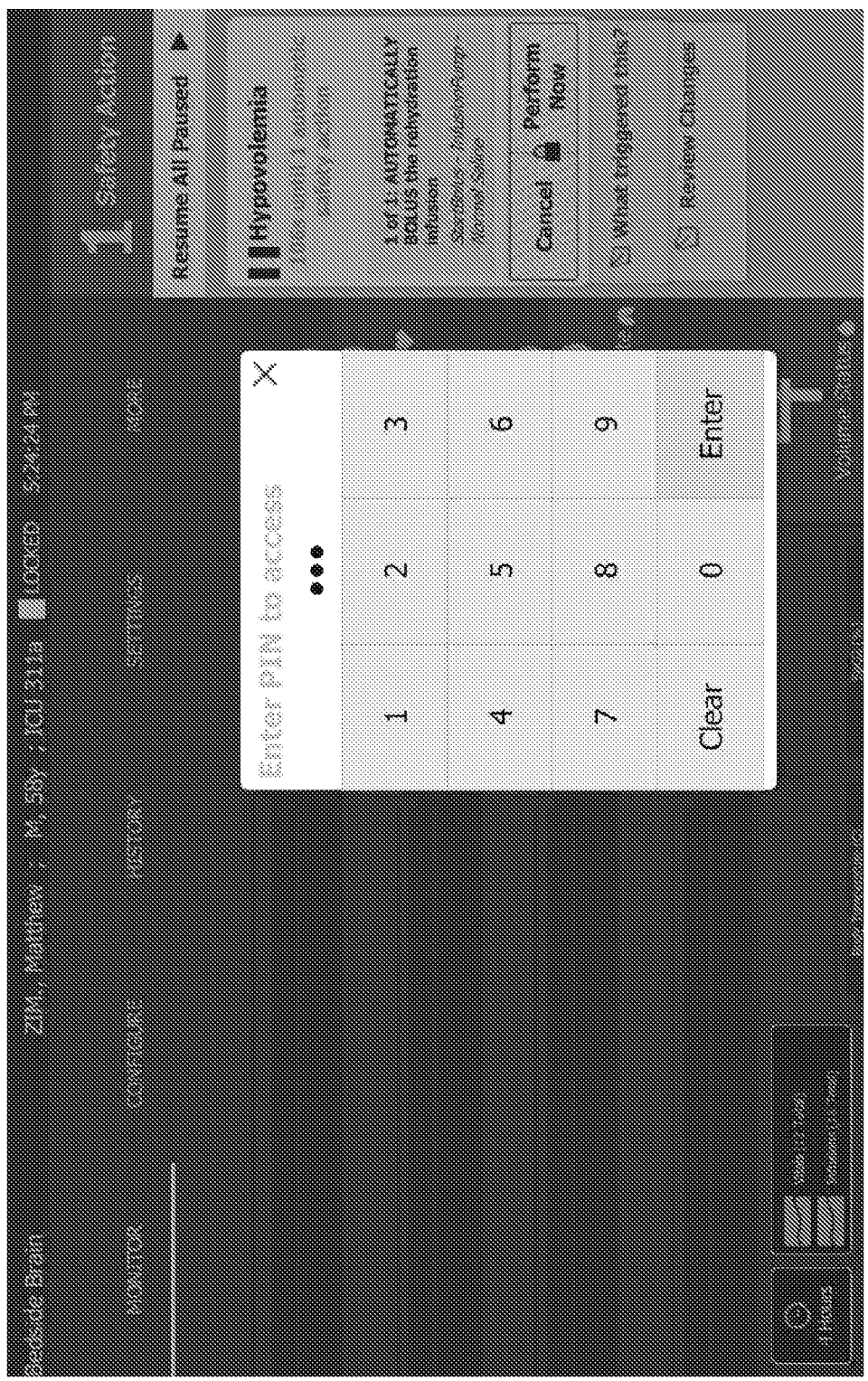
FIG. 20 is an illustration of a bedside brain interface requiring security to access a protocol while the protocol is running, according to an example embodiment of the present disclosure.

Alternatively or in addition to displaying a warning message, bedside brain 100 may proceed to take an additional action. FIG. 19 illustrates the interface of bedside brain 100 where the volume index for the patient 110 has remained at 4 (an unsatisfactory value). Per the protocol-specific settings (e.g., described with respect to FIGS. 4 and 12 above), bedside brain 100 will trigger the protocol specific action (e.g., "Safety Action"). For example, bedside brain 100 indicates the action that it will take, with the specific device (e.g., BOLUS the rehydration infusion" with "InfusionPump"). At this point, bedside brain 100 may trigger additional alarms (e.g., audible alarms, visual alarms, alarms to remote devices, etc.) to inform the user that an action will be taken. Bedside brain 100 starts a countdown to the auto-execute time (e.g., described above with respect to FIG. 8). While bedside brain 100 is counting down to the auto-execute time, the user may select Cancel or Perform Now as illustrated by FIG. 20. For example, responsive to the user selecting either option, bedside brain 100 displays a keyboard, such that the user can enter a PIN or other password to unlock bedside brain 100 and access the ability to Cancel or Perform Now. This advantageously ensures that unauthorized users cannot cancel or perform protocols on bedside brain 100.

Figure 21:
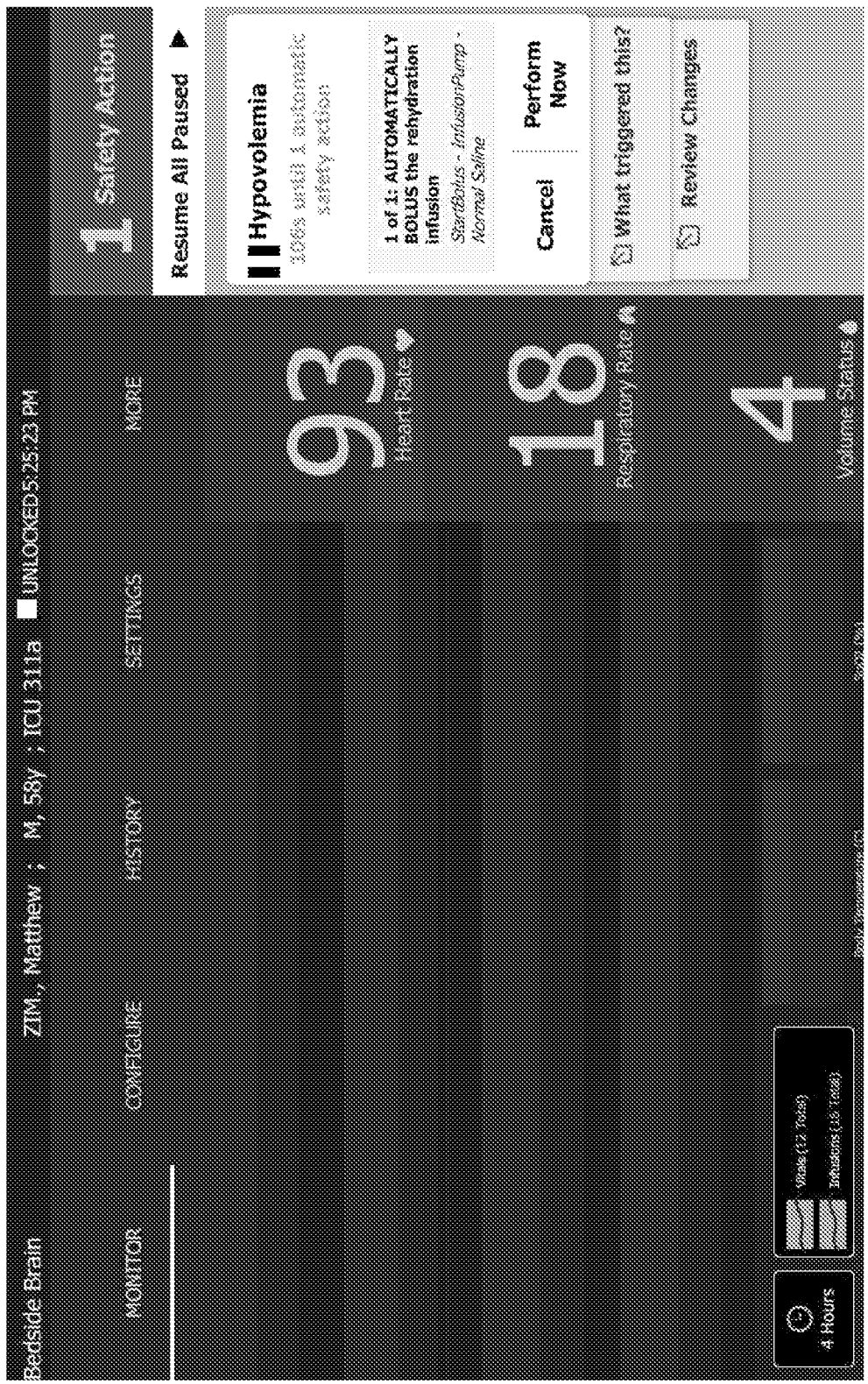
FIG. 21 is an illustration of a bedside brain interface displaying options for a safety action while a protocol is running, according to an example embodiment of the present disclosure.

FIG. 21 illustrates the interface of bedside brain 100, once unlocked by the user. For example, the user can select "Cancel," such that bedside brain 100 no longer configures patient therapy device 106A with the selected protocol. If canceled, the protocol configuration may be completely severed from the patient therapy device 106A. In other words, to re-activate the protocol, the user must go through all the steps previously described (starting at the description of FIG. 3). Alternatively, the user can select "Perform Now," such that bedside brain 100 immediately performs the action associated with the protocol. In the Hypovolemia protocol, the action is "Automatically Bolus" the rehydration infusion. For example, by selecting "Perform Now" on bedside brain 100, bedside brain 100 instructs patient therapy device 106A to bolus the patient 110 (with parameters defined previously, as in FIG. 12), and the patient therapy device 106A delivers the bolus to patient 110.

Figure 22:
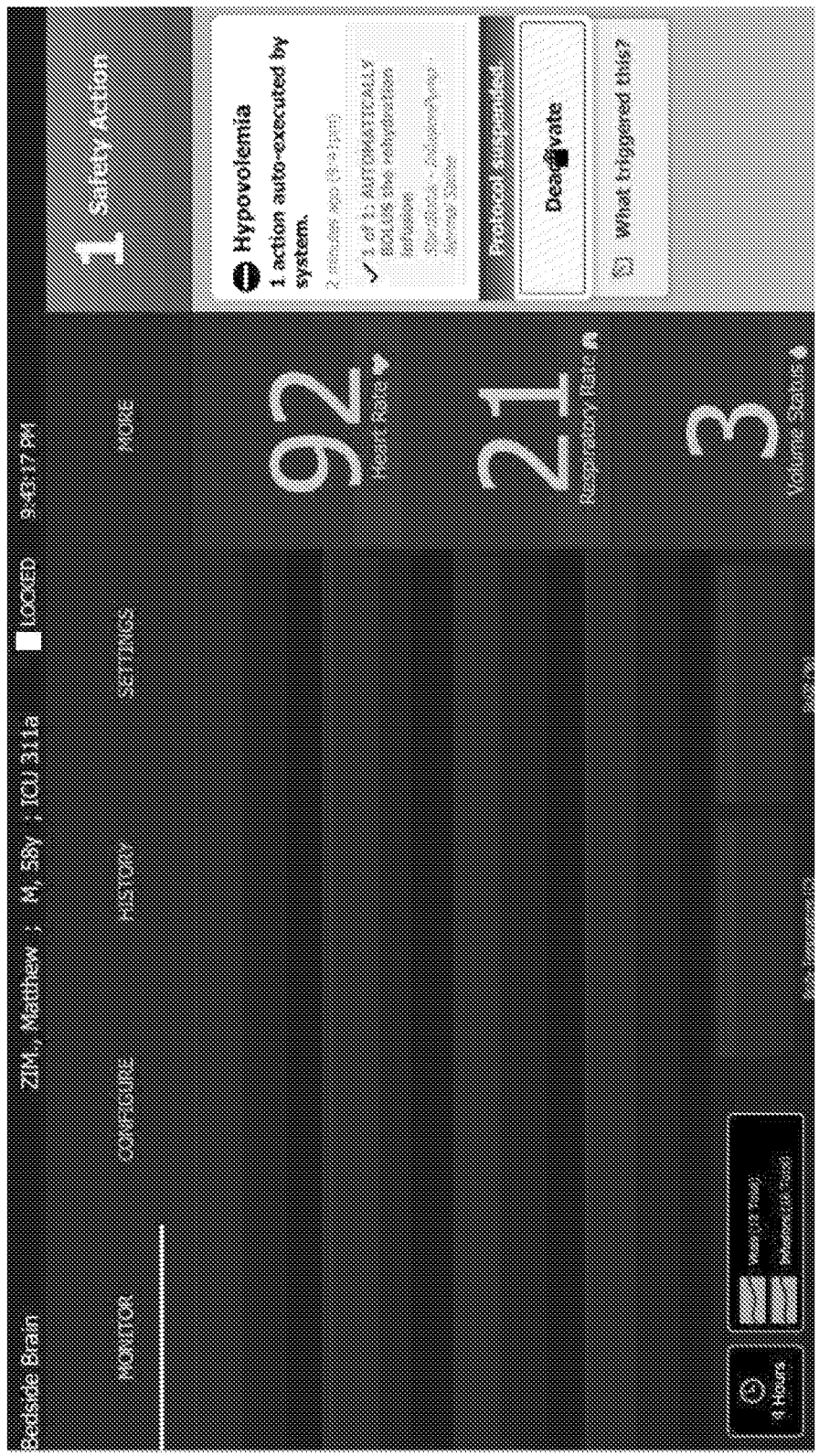
FIG. 22 is an illustration of a bedside brain interface displaying auto-execution of a safety action, according to an example embodiment of the present disclosure.

Alternatively, instead of selecting "Cancel" or "Perform Now," the user can wait for the auto-execute time to expire. FIG. 22 illustrates the interface of bedside brain 100, displaying auto-execution of the protocol. Most typically, this circumstance occurs if the user is out of the patient's room. In this situation, once the auto-execute time expires, bedside brain 100 takes the action dictated by the protocol as described above (e.g., "Automatically Bolus" the rehydration infusion). Thus, regardless of whether the user is aware of the warning message or that the bedside brain 100 intends to take the action, bedside brain 100 proceeds to take the action dictated by the protocol once the auto-execute time expires.

Also, similar to the cancellation description above, once the protocol is performed (e.g., via "Perform Now" or via auto-execute time expiry), the protocol configuration may be completely severed from the patient therapy device 106A. In other words, to re-activate the protocol, the user must go through all the steps previously described (starting at the description of FIG. 3). This ensures that a protocol is only performed once, if at all.

As an additional embodiment, there may be situations where, prior to the action being taken by bedside brain 100, the condition of patient 110 improves. For example, the interface of bedside brain 100 may display updated protocols. In this example, when compared to FIG. 18, the interface of bedside brain 100 may display that the volume index for patient 110 has improved from 4 (an unsatisfactory value) to 8 (a satisfactory value). Thus, per the protocol-specific settings (e.g., described with respect to FIGS. 4 and 12 above), bedside brain 100 no longer needs to take an action or show a warning message (e.g., volume index is not below 7 per the protocol). Though the protocol is no longer active, bedside brain 100 may include a history of what happened, or what triggered the protocol initially. In this way, the user can view a historical summary of any protocols triggered, based on undesirable or non-ideal patient physiological parameters.

Figure 23:
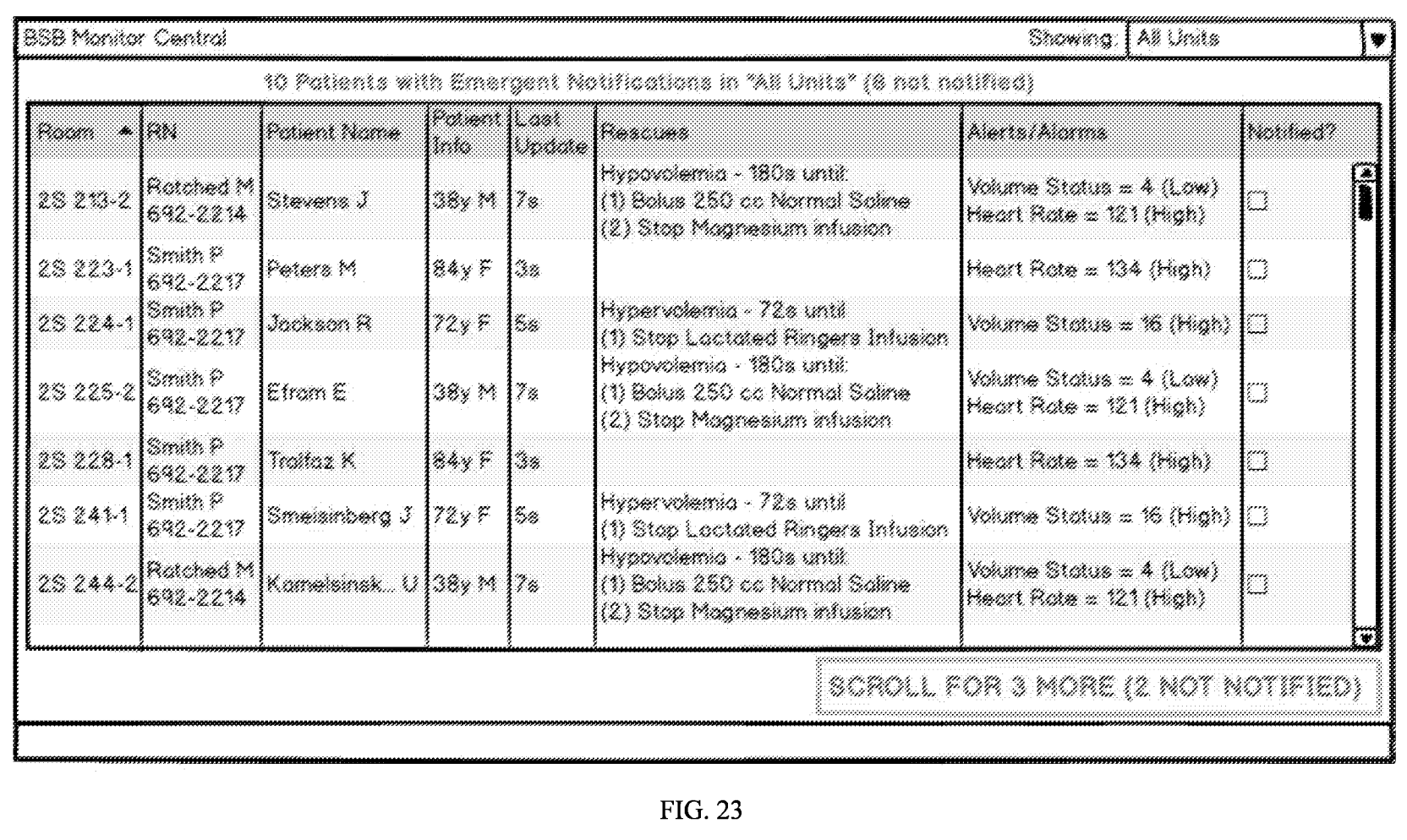

FIG. 23 illustrates the interface of a bedside brain central monitoring interface. Specifically, as previously noted, bedside brain server 102 may monitor the status of multiple bedside brains, such as in a hospital network (e.g., connected to the server). The bedside brain server 102 collects data sent by the bedside brain 100 connected to patient 110 (and additional bedside brains connected to additional patients) and provides analytic information (e.g., performance information, patient information, etc.). This information can be viewed and/or accessed from a central location, such as the central monitoring interface in FIG. 23. In this way, the user can identify the status of individual protocols across a number of bedside brains for a number of patients and related patient therapy devices 106A-B.

In an embodiment, bedside brain 100 affirmatively identifies therapy interruptions (e.g., a pump occlusion), and consequently triggers a therapy device alarm (e.g., pump occlusion indication), alerting the clinician, and modifying the therapy based on the therapy interruption. For example, the bedside brain 100 may change or update the flow of other medications (if needed) to maintain patient safety in lieu of a therapy interruption.

In an embodiment, bedside brain 100 affirmatively identifies normally occurring disturbances and accounts for these disturbances. For example, if the patient coughs, the bedside brain 100 identifies this impulse and takes it into account.

In an embodiment, bedside brain 100 affirmatively identifies patient input failure (e.g., vital sign monitor failure). The bedside brain 100 receives a monitor failure indication (e.g., ECG lead failure indication), alerts the clinician, and modifies the therapy (if needed) to maintain patient safety in lieu of the patient input failure.

In an embodiment, if the patient therapy device 106A cannot completely fulfill a protocol action, the patient therapy device 106A will, nonetheless, make a best effort to do so. For example, a protocol action instructs a pump to give a 500 cc bolus, which was initially possible when the protocol was first activated; but, now there is no longer 500 cc in the pump reservoir (e.g., only 300 cc remaining). The best effort is to administer the 300 cc and notify the bedside brain 100 of the shortfall. The bedside brain 100 would then proceed to notify the user of this shortfall (e.g., on the interface of bedside brain 100). In an embodiment, devices may continuously update individual capabilities list, for instance, if a drug is getting low, if a bolus beyond the volume required is no longer capable, etc. and send these capabilities lists to the bedside brain 100. Thus, bedside brain 100 can dynamically determine what protocols are available, given the resources at its disposal.

In an embodiment, the bedside brain 100 implements automated patient safety protocol by harmful therapy stoppage. For example, the bedside brain 100 may include both monitoring capabilities and application/decision support (e.g., contextual trends, protocol alerts, etc.). The bedside brain 100 may identify a harmful therapy and stop the harmful therapy (e.g., stopping the therapy device from infusing), and may perform additional safety protocol functions (e.g., infusing a drug to assist in patient safety protocol or physiological improvement).

Regarding stopping the therapy device from infusing, bedside brain 100 may additionally be connected to external devices, such as an electromechanical device that, on receipt of a command (wired or wireless) from bedside brain 100, clamps compressible hollow tubing (e.g., an intravenous catheter, a dialysis catheter, a foley catheter, oxygen tubing, and the like). In this way, the electromechanical device can effectively cut off the flow of contents through the flexible tubing. The electromechanical device can apply this safety feature (e.g., stop-flow) to any therapeutic device that has flexible tubing, without requiring additional direct communication with the therapeutic device. Rather, only communication with bedside brain 100 is needed. The electromechanical device can clamp the compressible hollow tubing via pinching, folding, squeezing, or other related means. The electromechanical device may employ a slide or roller clamp, a rotatable stopcock, or other related features. Similarly, the electromechanical device may unclamp a previously clamped hollow tube, thus reversing occluded flow and allowing the flow of contents through the flexible tubing.

In another embodiment, the bedside brain 100 implements automated patient safety protocol by therapy initiation or change. For example, the bedside brain 100 may include additional applications/decision support, additional algorithms, monitoring, and alerting capabilities, and may incorporate customer-created algorithms.

In another embodiment, the bedside brain 100 implements automated physiologic control. For example, the bedside brain 100 may include additional applications/decision support, additional algorithms, monitoring, and alerting capabilities, and may incorporate customer-created algorithms, in addition to physical control of devices (e.g., automatic vasopressor drip titration and fluid management). The bedside brain 100 may identify a harmful therapy, stop the harmful therapy, and perform safety protocol functions automatically.

Bedside Brain Protocol Customization

Bedside brain 100 may include a rule creation and validation tool, such that any additional actor or source, as noted above, can create rules to be implemented as protocols on bedside brain 100. Similarly, bedside brain 100 may communicate with a rules library, which can be a local library (e.g., stored on bedside brain 100) or an external library (e.g., accessed via BSB server 102, cloud 104, or the Internet). Thus, the features disclosed herein, including the rule creation and validation tool, may be accessed by the user on bedside brain 100, or remotely on an external computer.

Generally, a rule specification may provide the user with the particular required elements to configure the bedside brain 100 for a specified rule, to be implemented as a protocol. For example, the rule specification identifies the structure of the execution engine, required for an individual rule (e.g., the rules engine configuration specification). The rule specification identifies actions that get executed upon rule execution. The rule specification may be validated outside the bedside brain 100 (e.g., on the rule specification tool, on another bedside brain, etc.). In various embodiments, rule execution may occur as an ordered list, where each rule is executed separately or rule execution may be concatenated, such that a single device (with a single work flow) may executes several rules simultaneously.

Regarding the rule creation and validation tool (also referred to herein as the rule specification tool), the rule specification tool allows the user to build a particular rule to be implemented as a protocol. The rule specification tool provides a configurable execution engine that runs the rule. The execution engine for the individual protocol could be as simple as a liner function, or as complex as a trained artificial-intelligence engine based on a specific graph (e.g., FFT, wavelet Kalman filter, etc.). For example, the rule employs an if-then logic, prior to performing additional action. The execution engine and its constructs may run on a general processing unit and/or a sub-processor. The rule specification tool provides a simulation environment, which may allow validation of the rule against a test and validation database. The rule specification tool provides a mechanism to manage and distribute various rules (e.g., over the cloud server). The rule specification tool ensures that the final rule follows a set of strict formatting, content, and rule validity checks as dictated by the rule specification or requirements. The rule specification tool indicates if the rule does not conform to semantic and execution criteria.

Further, the bedside brain 100 will preferably verify that a selected rule conforms to pre-determined semantic and execution criteria. Likewise, the bedside brain 100 will preferably indicate if a rule does not conform to pre-determined semantic and execution critera, and not permit the rule to be activated as a protocol. Bedside brain 100 may further include internal run time diagnostics and safety mechanisms (e.g., watchdog timer, handshakes and check pointing of subsystems, safety segmentation, etc.). If the bedside brain 100 detects an internal error, it brings the system to a safe state, and alerts the clinician.

Rule specification creators, noted as additional actors, may be authorized representatives that can approve, create, and push rules to bedside brains (e.g., via the bedside brain server 102). Specifically, these additional actors may generate requirements for a given rule, establish criteria for treatment of a specific condition, use tools to create a rule to treat a specific condition, perform a validation of the rule using authorized tools, document the rule, and push the rule to the bedside brain server 102 for distribution to the bedside brain 100.

In an embodiment, the bedside brain 100 itself parses the protocol and guarantees the system will enable a protocol for possible activation if the protocol follows all proper syntax. In an embodiment, the bedside brain 100 accepts Arden syntax formatted rules. In an embodiment, the bedside brain 100 parses the protocol and understands the requirements of the protocol because it parsed what the protocol does by reading its algorithmic logic rather than relying on manually generated metadata elements that might be in conflict with the rule itself. In an embodiment, the bedside brain 100 may parse that to note if an input/output is optional without having to make that a manually-entered metadata item in the protocol. For example, if the bedside brain 100 identifies that a protocol conditional tests whether a sensor has been connected and/or configured, then that sensor may be optional. Likewise, the bedside brain 100 may allow optional inputs, as an alternative to parsing.

In an embodiment, the bedside brain 100 includes a semantic translator, such that the bedside brain 100 itself does not require any hard-coding related to any patient therapy device 106A-B. Regarding the semantic translator, it may include an editable configuration file (e.g., a location that enables mapping from one terminology to another). In this way, for example, if a sensor says that it is of type "ECG," but the rule specifies a sensor of type "EKG," and these two are the same thing, but for differing terminology, the configuration file enables a mapping of ECG to EKG (and vice versa) so that there is a layer of indirection between the syntax of the rule and the syntax sent by the device 106A-B.

Regarding therapeutic devices 106A-B, each therapeutic device 106A-B may be individually compatible with the bedside brain 100. For example, the device 106A-B may be required to follow certain behaviors, and follow any communications protocols required by the bedside brain 100. In an embodiment, upon connection (e.g., via hard-wire) between a therapeutic device 106A-B and the bedside brain 100, a handshaking occurs between the bedside brain 100 and the therapeutic device 106A-B. In an embodiment, handshaking includes identification, by the therapeutic device 106A-B: (1) that it is a therapeutic device, (2) what kind of device it is, (3) what non-therapeutic actions it can take, and (4) what therapeutic actions it can take.

Regarding sensors 108A-B, each sensor 108A-B may follow a particular protocol (e.g., IHE-PCD protocol) or some other common standard protocol. Likewise, as an alternative, the bedside brain 100 may include device drivers, for common proprietary devices 108A-B (e.g., GE and/or Phillips monitors). Preferably, device drivers will not be in the main source of code of the bedside brain 100.

In an embodiment, each protocol is independent of all other protocols. For example, no protocol may operate knowing or using the context of another protocol. A protocol may write data into the data store. This data, written by the protocol, may be readable only by the protocol (e.g., to ensure that protocols run independently of one another). Likewise, each "therapy" may only be controlled by a single protocol. The bedside brain 100 may restrict the user to enable a protocol if any of the protocol's potential actions include controlling a therapy that is already being controlled by another protocol. The bedside brain 100 may send the ID of the protocol requesting an action at the time it sends a request. For example, this allows the therapeutic device 106A-B itself to refuse to accept a command from the bedside brain 100 if it originates from a protocol that is different than the one which is already controlling.

More specifically, protocols may include a number of features. In an embodiment, protocols may include metadata. For example, protocols may define required user inputs, caption of said inputs, type of inputs, and allowed values for inputs and default values (if any) for inputs. Likewise, for example, protocols may include a description of the protocol and a name of the protocol, which will be user facing (e.g., in the user interface). Likewise, for example, protocols may include default values (e.g., default opt-out time). Likewise, for example, protocols may declare a protocol type (e.g., "safety protocol"). In an embodiment, protocols are configured to be simple, non-looping, if-then-else and/or if-else structures. As a result, protocols may be displayable in a flowchart or via other means, and readily understandable by users. In an embodiment, flowcharts may include descriptive aliases (e.g., for complex conditions), may eliminate nested conditionals in a single statement, or display other substitutes to improve user readability of the flowchart. In an embodiment, protocols have limited verbiage/characters to reduce the risk of protocols errors (e.g., due to hackers and/or bad writing). In an embodiment, if protocols include additional verbiage/characters, beyond the permitted limited verbiage/characters, the bedside brain may refuse to permit that protocol to be activated. In an embodiment, protocol conditionals may perform various operations. Protocol conditionals may perform simple operations available to the protocol via the syntax including arithmetic (e.g., multiply, divide, etc.) and logic (e.g., contains, starts with, etc.). For example, "if (HR<user_minimum*2) then." Protocol conditions may perform complex operations available to the protocol via system-given functions that are part of the syntax.

In an embodiment, protocol conditionals may also reference more arbitrary code that lives elsewhere in the syntax (e.g., a custom functions section). In an embodiment, since multiple different sensors 108A-B might provide the same data element (e.g., heart rate), the protocol should be able to specify if the data element must come from a specific source/sensor, or not. In an embodiment, the protocol should be able to have optional inputs or outputs. In an embodiment, syntax is a limited version of a standard programming language (e.g., Python), modified for simplicity to guarantee that the syntax has limited verbiage/characters. In a different embodiment, syntax is parsed as a brand new syntax.

Ideally, the bedside brain 100 may run any arbitrary protocol, so long as the protocol follows the proper syntax and any other rules, limitations, and requirements, mandated by the bedside brain 100 for a proper protocol. The bedside brain 100 itself checks the protocol and guarantees that the bedside brain will only enable a protocol for activation if the protocol follows the proper syntax and any other rules, limitations, and requirements, mandated for a proper bedside brain protocol. In an embodiment, multiple protocols may be run on one device and/or multiple devices simultaneously. Thus, the bedside brain 100 manages protocols, while interfacing with both a plurality of monitoring devices and a plurality of therapy devices.

In an embodiment, every connected device 106A-B/108A-B is considered an "input" (e.g., feeds data to the bedside brain) and some devices are considered "outputs"

(e.g., can perform an additional function or action), and a subset of outputs are considered patient therapy devices 108A-B (e.g., can deliver a therapy). In an embodiment, the bedside brain 100 connects to devices via a hard-wire. For example, hard-wire connection reduces cyber-risk and malware. Likewise, for example, hard-wire connection may ensure that individual sensors, therapeutic devices, and the bedside brain 100 are all associated with the same patient (e.g., in the same physical room as the patient).

In an embodiment, there are different types of therapy devices 106A-B. Some therapy devices 106A-B provide only one therapy at a time. For example, a basic infusion pump only infuses one medicine at a time. Some therapy devices 106A-B provide more than one therapy at a time. For example, a multi-channel pump may infuse multiple medicines at a time. Some therapy devices 106A-B may only have one instance of that device per patient. For example, only one ventilator is used with a single patient. Some therapy devices 106A-B may have multiple instances of that device per patient. For example, multiple infusion pumps may be used with a single patient. In an embodiment, "therapy" is the particular therapy provided by the particular device. For example, the therapy for a ventilator is ventilation; the therapy for an IV pump is the combination of infusion plus the specific medicine that is being infused.

In an embodiment, if a single device can and is configured to perform multiple therapies, the single device emulates one device per therapy in its communications with bedside brain 100. For example, a three-channel IV pump that has only one medication would emulate a single device and a single therapy. Likewise, for example, the three-channel IV pump has that all three channels hooked up to different medications would emulate three devices and three therapies (e.g., one medication per therapy). In this example, the three-channel IV pump would send three separate handshakes and three separate messages with each update of its status.

In an embodiment, a multitude of physiological parameters may be monitored with patient monitoring devices 108A-B. An exemplary listing of various physiological parameters is illustrated in Table 1 below. It should be noted that the inputs listed in Table 1 form a non-inclusive list. Many other inputs, besides those in Table 1, are contemplated by the bedside brain.

TABLE 1

Exemplary Inputs

| Input Parameter | Source | Type | Normal Range | Max Range | Representation in "rule" | Units | Description |
|---|---|---|---|---|---|---|---|
| Heart Rate | Instrument | Integer | 60-100 | | | BPM | Beats, QRS pulses per minute |
| SpO2 | Instrument | Float | 90-100 | | | Percent | Percentage of Oxygenated Hemoglobin |
| Systolic Arterial Pressure | Instrument | Integer | 90-140 | | | mmHg | Usually included in "vital signs" |
| Diastolic Arterial Pressure | Instrument | Integer | 60-90 | | | mmHg | Usually included in "vital signs" |
| Mean Arterial Pressure | Instrument | Integer | 70-100 | | | mmHg | Calculated value |
| Respiratory rate | Instrument | Integer | 12-40 | | | 1/min | Age dependent (highest for newborns) |
| Body temperature | Instrument | Float | 98-98.6 | | | Deg. F | Usually included in "vital signs" |
| Lactate | Lab | Float | 0.5-1.0 | | | mmol/L | High lactate may indicate hypoperfusion. Sepsis related biochemical variable |
| Base deficit | Lab | Float | −2.0-2.0 | | | mEq/L | Sepsis related biochemical variable. Metabolic alkalosis if too high, metabolic acidosis if too low |
| Serum glucose level | Lab | Integer | <125 | | | mg/dL | Blood sugar |
| Serum bicarbonate level | Lab | Integer | 22-29 | | | mmol/L | Total amount of carbon dioxide |
| Serum ketone level | Lab | Float | <1.0 | | | mg/dL | Blood acids; elevated may indicate ketoacidosis |
| pH | Lab | Float | 7.35-7.45 | | | | pH of arterial blood; less than 7.3 may indicate ketoacidosis |

TABLE 1-continued

Exemplary Inputs

| Input Parameter | Source | Type | Normal Range | Max Range | Representation in "rule" | Units | Description |
|---|---|---|---|---|---|---|---|
| GFR | Lab | Float | 60< | | | mL/min/ 1.73 m2 | Very low may indicate kidney failure |
| Serum creatinine | Lab | Float | 0.6-1.3 | | | mg/dL | Rise may indicate kidney failure |
| Urine output | Instrument | Float | 0-10 | | | L | Decrease may indicate kidney failure |
| ECG | Instrument | Analog | | | | | 12 lead |
| WBC count | Lab | Integer | 3500-10500 | | | cells/ microliter | Obtained from complete blood count test (CBC) |
| Platelet count | Lab | Integer | 150000-45000 | | | 1/microliter | Obtained from complete blood count test (CBC) |

Use Case Examples

As previously described, the bedside brain 100 allows a clinician to set ranges for input values, derived values, device settings, and other data points and may perform therapy related to a specific safety protocol. An example below illustrates a protocol for a hyperkalemia rule.

TABLE 2

Exemplary Hyperkalemia Rule

| | |
|---|---|
| Rule Name | Hyperkalemia Safety Protocol |
| Rule Revision | 1 |
| Rule Type | Safety Protocol, One shot rule required user to re enable |
| Opt Timeout Default | 2 Min |
| Patient Information Required Asked at rule selection | None |
| List of adjustable rule parameters: Asked at rule selection | One tuple for each rule specific adjustable parameter |
| Patient Rule Specific Parameters | HR_MIN_PT_HYPERKALEMIA, defaults to HR_MIN_HYPERKALEMIA |
| Patient Rule Specific Parameter Text | "Set the minimum allowable heart rate for Hyperkalemia:" |
| Patient Specific Rule Parameter allowable range | 40 < hyperkalemia mon heart rate < 70 |
| Input Validation Rule | Specify and input validation rule |
| Required Input Device List | ECG<br>Heart Rate<br>(ecg.heart_rate, AND (spo2.heart_rate OR piva.heart_rate)) |
| Required Output Device List | Pump_1: Potassium, Action shutoff<br>Pump2: BiCarbonate, Action Deliver bolus, Bolus Volume |
| Output Guard Rails | (No potassium guard rail required shut off only)<br>Bicarb Volume Guard Rail Mac Volume = XXX mL |
| Alarm Settings Input Parameters | None |
| Conditions for selection enabled | (ECG_VALID AND (HR_VALID_ECG OR HR_VALID_SPO2) AND (PUMP_1_RUNNING AND PUMP_1_DRUG == POTASSIUM) AND (PUMP_2_STANDBY AND PUMP_2_DRUG == BICARBONATE)) (AND NOT ANY_PUMP_DELIVERING_EPI) |
| Rule, Actions may be in the rule. | See below |
| Therapeutic Actions Lis | Pump1.potasium OFF<br>Pump2.bicarb deliver bolus volume |
| Non Therapeutic Actions List | None |
| Alarm Actions List | CFH rule |

The related rule logic for the Exemplary Hyperkalemia Rule includes:

```
IF (NOT ANY_PUMP_DELIVERING_EPI) //This is a basic drug safety check
    IF (ECG_FAULTED AND HEART_RATE_ECG_INVALID) // Required inputs are
    both faulted
        ACTION: CFH_RULE
```

```
            NOTE: here the unit sits in the fault state, can the CFH get turned off?
            Consideration of always having to reset the alarm manually with no automatic
            reset.
        ELSEIF (ECG_FAULTED AND HEART_RATE_VALID) AND ( (HEART_RATE <
        HR_MIN_PT_HYPERKALEMIA) OR (HEART_RATE < HEART_RATE_BASELINE
        * 0.6))
            ACTION: CHF_RULE
            ACTION: TURN OFF POTASIUM
        ELSEIF      (QRS_WIDTH > QRS_WIDTH_MAX_HYPERKALIMIA) OR
        (QRS_WIDTH > (QRS_WIDTH_BASLINE * 1.25))
            AND
            ((HEART_RATE < HR_MIN_PT_HYPERKALEMIA) OR (HEART_RATE <
        HEART_RATE_BASELINE * 0.6)
            AND
            ( ALGO_QRS_PEAKING_PRESENT( ) OR
        QRS_PEAKING_GET_LEVEL_BASELINE * 1.25) // In this context, with an algorithm
                ACTION: CHF_RULE
                ACTION: TURN OFF POTASIUM
                ACTION: DELIVER BICARB
        ENDIF
ELSE
    ACTION: CHF_RULE
    SHOW DIALOG INDICATE SLECTION OF HYPERKALEMIA WHILE EPI
DELIVERY
ENDIF
```

For example, patient 110 is on a telemetry unit 106A and is receiving an IV administration of potassium via an infusion pump 108A. The patient's T-waves become peaked, the QRS complex starts to widen, and the patient's 110 heart rate decreases. These are some typical signs of hyperkalemia. Bedside brain 100 reads the patient data and recognizes this pattern, via the "typical signs" just noted. Bedside brain 100 sounds an alarm, paging a nurse, doctor, or other emergency healthcare provider. Unfortunately, no one answers the alarm. Bedside brain 100 executes a safety protocol: it stops the IV potassium administration. Additionally, in particular embodiments, bedside brain 100 may perform additional follow-up safety protocols, such as injecting an ampule of sodium bicarbonate (or calcium chloride if the patient is not on digoxin). To summarize, bedside brain 100 will stop a potassium infusion if the electrocardiogram of patient 110 shows signs of dangerously high potassium.

In a second example, a safety protocol relates to a hypotension rule. For example, a post-surgical patient 110 is recovering, but starts hemorrhaging internally. Bedside brain 100 predicts hypotension, by receiving inputs of respiratory rate, heart rate, volume-status signal, and derived values via subnodes in the algorithm of heart rate variability, respiratory rate variability, and rate of change of volume-status. Bedside brain 100 calls for help, but no one responds. Then the patient's 110 volume-status signal actually indicates hypotension. Bedside brain 100 gives an IV bolus of 500 cc of Lactated Ringer's solution to the patient 110, pages the physician, pages the nurse, and continues to alarm audibly.

In a third example, a safety protocol relates to identifying fluid overload. For example, a patient 110 in the emergency department is receiving IV fluids for dehydration, because patient 110 has the flu. Bedside brain 100 identifies that patient 110 is becoming fluid overloaded, based on the patient's 110 volume-status signal, and that the patient's 110 respiratory rate is also increasing. Bedside brain 100 considers those factors, as related to the IV fluid infusion, and calls for help, but no one responds. Bedside brain 100 reduces the IV fluid infusion rate, pages the physician, pages the nurse, and continues to alarm audibly.

In a fourth example, a safety protocol relates to predicting hypotension. For example, patient 110 is receiving hemodialysis in the intensive care unit. Bedside brain 100 identifies hypotension, using inputs of respiratory rate, heart rate, volume-status signal, and derived values via subnodes in the algorithm of heart rate variability, respiratory rate variability, and rate of change of volume-status. Bedside brain 100 calls for help, but no one responds. Bedside brain 100 automatically reduces dialysis to its slowest possible rate, pages the nurse, pages the physician, and continues to alarm audibly.

In a fifth example, a safety protocol relates to predicting hemorrhaging. For example, patient 110 is put on low-molecular weight heparin shots, for a blood clot issue, despite significant concerns that the patient 110 might hemorrhage. Bedside brain 100 notes an increased heart rate, increased respiratory rate, and low volume-status. Bedside brain 100 calls for help, but no one answers. Bedside brain 100 may initiate two actions: infusing a bolus of 250 cc saline and a starting a slow push of IV protamine sulfate (e.g., to partially reverse the heparin shots).

It should be appreciated that the examples provided above are not limiting, and that the bedside brain can perform many other safety protocol actions with many other sensors and therapeutic devices.

It will be appreciated that all of the disclosed methods and procedures described herein can be implemented using one or more computer programs or components. These components may be provided as a series of computer instructions on any conventional computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

As used in this specification, including the claims, the term "and/or" is a conjunction that is either inclusive or exclusive. Accordingly, the term "and/or" either signifies the presence of two or more things in a group or signifies that one selection may be made from a group of alternatives.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention is claimed as follows:

1. A system comprising:
   a memory;
   one or more processors, in communication with the memory;
   a plurality of medical therapy devices;
   a plurality of patient monitoring devices; and
   a protocol execution module, configured to execute on the one or more processors, to:
     display a plurality of protocols, wherein the plurality of protocols is dictated by an individual medical therapy device, such that each of the plurality of protocols are configured to be ran on the individual medical therapy device, the individual medical therapy device being one of the plurality of medical therapy devices;
     receive, from a user, a selected protocol of the plurality of protocols, the selected protocol associated with the individual medical therapy device and associated with an individual patient monitoring device, being one of the plurality of patient monitoring devices;
     display the selected protocol, such that an entire logical flow of the selected protocol is displayed in a user-readable format including each possible logical determination and related action to be taken;
     receive, from the user, a plurality of common settings for the selected protocol;
   wherein the individual medical therapy device is configured to receive, from the user, a first confirmation of the selected protocol,
   wherein the protocol execution module is configured to receive, from the user, a second confirmation of the selected protocol,
   such that the protocol execution module is configured to execute the selected protocol with the individual medical therapy device.

2. The system of claim 1, wherein the plurality of medical therapy devices includes at least one of an infusion pump, a dialysis or renal failure therapy machine, a respirator, and a defibrillator.

3. The system of claim 1, wherein the plurality of patient monitoring devices includes at least one of a heart rate sensor, a temperature sensor, a pulse oximetry sensor, a patient weight sensor, a glucose sensor, a respiratory sensor, a blood pressure sensor, a pressure sensor, and a volume-index sensor.

4. The system of claim 1, further comprising an external server, wherein the protocol execution module is configured to receive the plurality of protocols from the external server.

5. The system of claim 1, wherein executing the selected protocol with the individual medical therapy device includes:

identifying a patient parameter with the individual patient monitoring device; and
determining that the patient parameter violates a threshold, wherein the threshold is dictated by the selected protocol.

6. The system of claim 5, wherein executing the selected protocol with the individual medical therapy device further includes, responsive to determining that the patient parameter violates the threshold, triggering an alarm.

7. The system of claim 6, wherein, responsive to triggering the alarm, the system is configured for displaying, at the protocol execution module, an action dictated by the selected protocol.

8. The system of claim 7, wherein the system is configured for starting a countdown timer.

9. The system of claim 8, wherein the system is configured such that, when the countdown timer expires, the protocol execution module instructs the individual medical therapy device to take the action, and the individual medical therapy device takes the action.

10. The system of claim 9, wherein the individual medical therapy device is an infusion pump, and wherein the action is one of increasing an infusion rate of the infusion pump, decreasing an infusion rate of the infusion pump, and ceasing infusion.

11. The system of claim 9, wherein executing the selected protocol with the individual medical therapy device further includes, responsive to the countdown timer expiring, triggering an alarm.

12. The system of claim 8, wherein the system is configured such that, prior to the countdown timer expiring, the protocol execution module can be instructed by the user to take the action, and the protocol execution module instructs the individual medical therapy device to take the action, such that the individual medical therapy device takes the action.

13. The system of claim 8, wherein the system is configured such that, prior to the countdown timer expiring, the protocol execution module can be instructed by the user to cancel the action, such that the protocol execution module pauses the countdown timer and removes the action from the individual patient monitoring device such that the first confirmation no longer exists.

14. The system of claim 8, wherein the system is configured for, prior to the countdown timer expiring:
   identifying an updated patient parameter with the individual patient monitoring device;
   determining that the updated patient parameter no longer violates the threshold; and
   removing the action from the selected protocol, such that the action is no longer displayed at the protocol execution module.

15. The system of claim 1, wherein the plurality of common settings for the selected protocol include at least one of an expiration time for the selected protocol, a delay time for the selected protocol, and a delay time for taking an action.

16. The system of claim 1, wherein every protocol in a protocol listing includes at least a call for help rule, such that, responsive to determining that a patient parameter violates a threshold, an alarm is triggered.

* * * * *